(12) United States Patent
Cornsweet et al.

(10) Patent No.: US 10,463,248 B2
(45) Date of Patent: Nov. 5, 2019

(54) SYSTEMS, METHODS, AND DEVICES FOR MEASURING EYE MOVEMENT AND PUPIL RESPONSE

(71) Applicant: Brien Holden Vision Institute, Sydney (AU)

(72) Inventors: Tom N. Cornsweet, Prescott, AZ (US); Paul Peterson, Prescott, AZ (US); Brad Bower, Hillborough, NC (US)

(73) Assignee: Brien Holden Vision Institute Limited, Sydney NSW (AU)

( * ) Notice: Subject to any disclaimer, the term of this patent is extended or adjusted under 35 U.S.C. 154(b) by 0 days.

(21) Appl. No.: 15/117,995

(22) PCT Filed: Feb. 10, 2015

(86) PCT No.: PCT/US2015/015179
§ 371 (c)(1),
(2) Date: Aug. 10, 2016

(87) PCT Pub. No.: WO2015/120438
PCT Pub. Date: Aug. 13, 2015

(65) Prior Publication Data
US 2017/0007119 A1    Jan. 12, 2017

Related U.S. Application Data

(60) Provisional application No. 61/937,788, filed on Feb. 10, 2014.

(51) Int. Cl.
*A61B 3/14* (2006.01)
*A61B 3/10* (2006.01)
(Continued)

(52) U.S. Cl.
CPC ............ *A61B 3/113* (2013.01); *A61B 3/0025* (2013.01); *A61B 3/0058* (2013.01);
(Continued)

(58) Field of Classification Search
CPC ............ A61B 3/113; A61B 3/103; A61B 3/14; A61B 3/1225; A61B 3/024; A61B 3/032; A61B 3/1015; G02C 5/00
(Continued)

(56) References Cited

U.S. PATENT DOCUMENTS

| 5,070,883 | A | | 12/1991 | Kasahara | |
| 5,495,305 | A | * | 2/1996 | Martin | A61F 9/00 351/159.75 |

(Continued)

FOREIGN PATENT DOCUMENTS

JP    2001321342    11/2001

OTHER PUBLICATIONS

International Search Report dated May 15, 2015 for PCT/US2015/015179.

*Primary Examiner* — Dawayne Pinkney
(74) *Attorney, Agent, or Firm* — Jones Day

(57) ABSTRACT

A device for monitoring eye movement and pupil response that comprises a first optical pathway for displaying one or more images to the eyes of a patient and a second optical pathway for obtaining images of the eyes of a patient. The device further comprises at least one screen for displaying an image to the left eye of the patient which is not visible to the right eye of the patient and for displaying an image to the right eye of the patient which is not visible to the left eye of the patient; a first camera for capturing images of the left eye of the patient; and a second camera for capturing images of the right eye of the patient at substantially the same time as the first camera is capturing images of the left eye of the patient. The device also comprises at least one IR light source for illuminating the eyes of the patient; and a processor for processing the obtained images and measuring pupil response and/or eye movements.

22 Claims, 5 Drawing Sheets

(51) Int. Cl.
*A61B 3/02* (2006.01)
*A61B 3/00* (2006.01)
*A61B 3/113* (2006.01)
*A61B 3/11* (2006.01)
*A61B 3/12* (2006.01)
*A61B 5/00* (2006.01)

(52) U.S. Cl.
CPC ............ *A61B 3/0091* (2013.01); *A61B 3/112* (2013.01); *A61B 3/1216* (2013.01); *A61B 3/14* (2013.01); *A61B 5/4064* (2013.01)

(58) Field of Classification Search
USPC ....... 351/210, 200, 205, 206, 209, 221–223, 351/246, 41
See application file for complete search history.

(56) References Cited

U.S. PATENT DOCUMENTS

| | | |
|---|---|---|
| 6,386,706 B1 | 5/2002 | McClure et al. |
| 2002/0099305 A1 | 7/2002 | Fukushima et al. |
| 2004/0105075 A1* | 6/2004 | Kandel ................. A61B 3/112 351/221 |
| 2004/0233061 A1 | 11/2004 | Johns |
| 2005/0024586 A1* | 2/2005 | Teiwes .................. A61B 3/113 351/209 |
| 2006/0204041 A1* | 9/2006 | Hammoud ............ G08B 21/06 382/107 |
| 2009/0153796 A1* | 6/2009 | Rabner ................ A61B 3/0091 351/201 |
| 2009/0174865 A1* | 7/2009 | Privitera ............... A61B 3/112 351/246 |
| 2012/0008091 A1 | 1/2012 | Stewart |
| 2012/0081666 A1 | 4/2012 | Kinderman et al. |
| 2013/0176534 A1 | 7/2013 | Frankfort et al. |
| 2013/0278899 A1 | 10/2013 | Waldorf et al. |
| 2015/0073816 A1* | 3/2015 | Ha ..................... G06F 19/3481 705/2 |
| 2015/0190050 A1* | 7/2015 | Samadani .............. A61B 3/113 600/558 |
| 2015/0286070 A1* | 10/2015 | Aikawa ................ G02C 7/025 351/159.76 |
| 2015/0338915 A1* | 11/2015 | Publicover ......... H04N 5/23229 345/633 |
| 2016/0235295 A1* | 8/2016 | Sadhasivam ........... A61B 3/112 |

* cited by examiner

SYSTEMS, METHODS, AND DEVICES FOR MEASURING EYE MOVEMENT AND PUPIL RESPONSE

CROSS REFERENCE TO RELATED APPLICATION

This application is the National Phase application of International Application No. PCT/US2015/015179, filed Feb. 10, 2015, which designates the United States and was published in English, which claims priority to U.S. Provisional Application No. 61/937,788, filed Feb. 10, 2015. These applications, in their entirety, are incorporated herein by reference.

TECHNICAL FIELD

This document generally relates to systems, methods, and devices for measuring eye movement and pupil response. More specifically, this disclosure relates systems, methods, and devices for measuring eye movement and pupil response for identifying patient pathologies.

BACKGROUND

The neural pathways and centers that control eye movement and pupil response are extensive and broadly distributed throughout the volume of the brain. In addition, in healthy individuals, eye movements are precise. As a result, some disorders, such as Parkinson's disease, brain tumors, strokes, and trauma often produce abnormalities in some aspect of eye movements and/or pupil responses.

Currently, devices that are capable of identifying abnormalities in eye movements and/or pupil response in order to identify and/or diagnose pathologies, have significantly limited capabilities.

Accordingly, what is desired are systems, methods, and devices for measuring eye movement and pupil response to identify and/or diagnose pathologies.

SUMMARY OF EMBODIMENTS

Exemplary embodiments may provide a device that generates one or more stimuli to either or both eyes while continuously and precisely measuring the resulting eye movements and pupil responses. In exemplary embodiments, the resulting eye movements and pupil responses may be analyzed by a processor to identify and/or diagnose pathologies. In exemplary embodiments, the analysis may be performed in real time or substantially real time.

Exemplary embodiments may provide a device for monitoring eye movement and pupil response, the device comprising: a first optical pathway for displaying one or more images to the eyes of a patient; a second optical pathway for obtaining images of the eyes of a patient; at least one screen for displaying an image to the left eye of the patient which is not visible to the right eye of the patient and for displaying an image to the right eye of the patient which is not visible to the left eye of the patient; a first camera for capturing images of the left eye of the patient; a second camera for capturing images of the right eye of the patient, at substantially the same time as the first camera is capturing images of the left eye of the patient; at least one IR light source for illuminating the eyes of the patient; and a processor for processing the obtained images and measuring pupil response and/or eye movements.

In exemplary embodiments, the pupil response may comprise looking at the size of both pupils to determine how well the pupil responses are synchronized and/or the directions of gaze of one or both eyes to determine how well the movements of the eyes are synchronized.

In exemplary embodiments, the processing may further comprise determining the latency of the pupil response and/or eye movements.

In exemplary embodiments, the processing may further comprise determining the acceleration of the pupil response and/or eye movements.

In exemplary embodiments, the processing may further comprise distinguishing between translations and rotations of the eye.

In exemplary embodiments, the device may be capable of simulating macular degeneration.

In exemplary embodiments, the processor may use Hough transforms to track eye movements.

In exemplary embodiments, the device may further comprise at least one memory for storing a catalog of pathologies.

In exemplary embodiments, the processor may be configured to measure the relative sensitivities of the left and right retinas of the eyes.

In exemplary embodiments, the processor may be configured to measure the maximum velocity of pupil restriction.

In exemplary embodiments, the processor may be configured to measure a baseline set of pupil properties and/or responses of the pupils on a single subject, defining a set of predetermined baseline properties for comparison with later measurements.

In exemplary embodiments, a collection of population norms may be collected and stored.

In exemplary embodiments, the measurement may be compared with a baseline measurement on the same subject or with population norms.

In exemplary embodiments, the processor may be configured to measure the differences between predetermined properties and/or responses of the pupils.

In exemplary embodiments, the processor may be configured to compare predetermined properties of pupils to a set of predetermined population data.

In exemplary embodiments, the processor may be configured to compare the pupil response to convergence to a set of predetermined population data.

In exemplary embodiments, the processor may be configured to detect floppy iris.

In exemplary embodiments, the processor may be configured to compare pupil perimetry data to a set of predetermined population data.

In exemplary embodiments, the device may be configured to perform a fatigue test separately for each eye.

In exemplary embodiments, the device may be configured to measure and/or detect any plurality of the following: amplitude of a saccadic movement, maximum velocity of a saccadic movement, latency of a saccadic movement, accuracy of a saccadic movement, and/or direction of a saccadic movement.

In exemplary embodiments, the device may be configured to provide a target which moves in a predetermined pattern while measuring the smoothness with which the eyes track the target.

In exemplary embodiments, the device may be configured to measure the amount of scattering of light attributable to cataracts in the eye.

Exemplary embodiments may provide a device for identifying concussions, the device comprising: a first optical pathway for displaying one or more images to the eyes of a patient; a second optical pathway for obtaining images of the eyes of a patient; at least one screen for displaying an image to the left eye of the patient which is not visible to the right eye of the patient and for displaying an image to the right eye of the patient which is not visible to the left eye of the patient; a first camera for capturing images of the left eye of the patient; a second camera for capturing images of the right eye of the patient, at substantially the same time as the first camera is capturing images of the left eye of the patient; at least one IR light source for illuminating the eyes of the patient; and a processor for processing the obtained images and measuring pupil response and/or eye movements and comparing the pupil response and/or eye movements to similar data obtained from the same patient as a baseline measurement, wherein the processor is further configured to identify in substantially real-time whether the patient has a concussion based on predetermined differences between the baseline measurement and the current measurements.

DESCRIPTION OF THE DRAWINGS

Exemplary embodiments will now be described, by way of example only, with reference to the accompanying drawings in which.

DETAILED DESCRIPTION OF EXEMPLARY EMBODIMENTS

Figure 1:
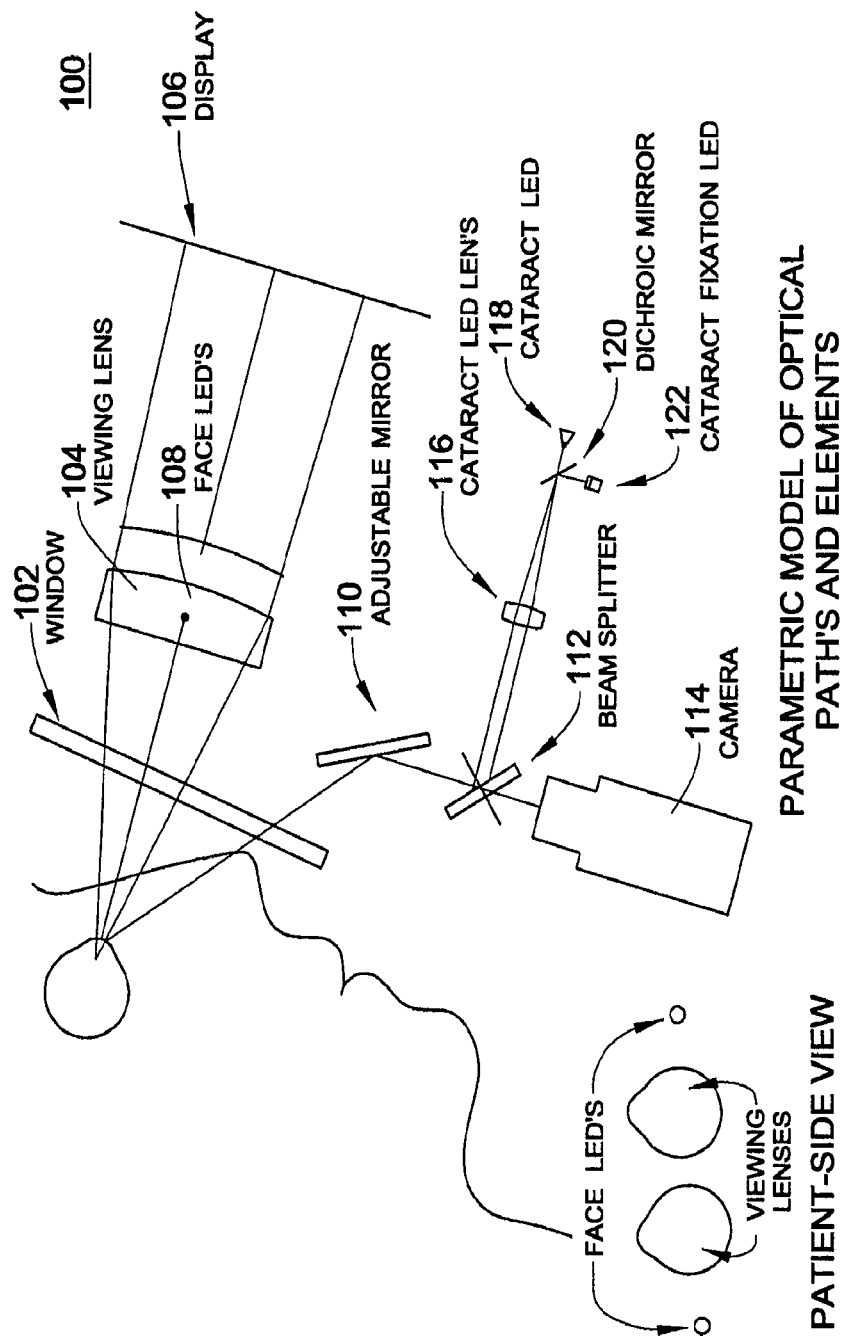
FIG. 1 is a schematic diagram of an exemplary device for use in measuring eye movement and/or pupil response.

The exemplary embodiments described herein include a number of optical elements or components, many of which, as individual elements, may be conventional in at least one of construction and/or operation. These components, we appreciate, may be incorporated, properly collaboratively combined, in modified embodiments of the system of the invention, with these components possessing a wide variety of recognized, readily user-chooseable, and fully satisfactory, optical characteristics. Accordingly, details of these several elements, except to the extent believed necessary to convey a clear understanding of how the systems, devices, and methods perform, may not be discussed in detail. Rather, the disclosure will rely appropriately on the knowledge and skill of those generally skilled in the art of optics, and on the below-described, fully-informative operational description of systems, devices, and methods, as being entirely adequate to enable those skilled in the art to build and use the exemplary embodiments.

In exemplary embodiments, a device that generates one or more stimuli to either or both eyes while continuously and/or precisely measuring the resulting eye movements, gaze angle, pupil responses, and/or the state of the pupil may be provided. The resulting eye movements and pupil responses may be analyzed by a processor to identify and/or diagnose pathologies and the analysis may be performed in real time or substantially real time.

In exemplary embodiments, clinical information can be gathered from eye movements and pupil responses. The clinical utility of this quantitative data can provide incremental diagnostic information into the diagnosis, treatment, and/or management of both injury and disease of the brain and visual system. These may include mild traumatic brain injury (mTBI or concussion), Alzheimer's disease, Huntington's disease, brain tumors, and glaucoma to name a few. Alternative diagnostic methods for these conditions may be subjective (e.g., in the case of neurocognitive testing for concussion) or have large footprints, are expensive and limited in access (e.g., magnetic resonance imaging [MRI] or computed tomography [CT] scans). In mTBI, for example, there is a need for an objective and quantitative testing system that can be performed at the site of injury, longitudinally track the natural history of the condition, and provide reproducible quantitative comparisons. Comparisons of pilot datasets from healthy patients with ophthalmological or neurological pathology may reveal important differences in eye movements and pupil responses indicative of the presence of disease or trauma.

Without being limited to any particular theory, it is believed that there are many parts of the brain that are actively engaged in the process of vision, and probing the eye and brain through visual stimuli and response experiments may provide a window into the functioning of the brain. The observables that can be measured in response to a visual stimulus include, without limitation, fast eye movements, or saccades, smooth pursuit eye movements, vergence, and changes in pupil size and shape. From those observed features, many useful metrics can be derived including: saccade accuracy (how close the gaze was to the target position at the end of the saccade), saccade latency (how much time elapsed between target motion and the initiation of the saccade), saccade maximum velocity; smooth pursuit error (how well the eye tracked the position of the target or how often the pursuit broke down into saccades); relative saccadic response differences; and pupil metrics such as pupil dilation and/or constriction velocity, pupil constriction latency, and relative pupil response (a comparison of the pupil response in the stimulated eye and the consensual response in the fellow, unstimulated eye).

Humans make approximately three saccadic eye movements per second, 170,000 saccades per day and about 5 billion in an average lifetime. A saccade is a quick, simultaneous movement of both eyes in the same direction. Saccadic eye movements adjust the location of the observed scene on the retina, which is an important step in how the eye and brain work together to process a visual scene.

Saccades occur when viewing both stationary and dynamically changing scenes and, along with smooth pursuit eye movements, play an important role in maintaining fixation on a moving target. Object tracking may rely on a broadly distributed neural system. Areas of the brain involved in saccadic eye movement include the oculomotor complex, the superior colliculus (SC) of the midbrain, and the cortical areas V1, V2, the lateral intraparietal sulcus (LIP), the frontal eye fields (FEF) and the medial eye fields (MEF). Visual pursuit may also involve cognitive processes such as selection of the target, anticipation, attention and spatiotemporal memory. Pupil constriction and dilation are controlled by parasympathetic and sympathetic pathways, respectively, and may be governed by the hypothalamic nuclei.

Traumatic brain injury (TBI) or concussion, is a significant public health concern with estimates ranging widely from 1.7 million to 8 million people affected annually in the US at a cost of over $60 million. Approximately 70-80% of TBI is classified as mild TBI (mTBI).

mTBI may have primary and secondary effects on the brain. For example, primary mTBI may be caused by acceleration, deceleration, and rotational mechanical forces. While linear acceleration and deceleration may cause superficial trauma to grey matter resulting in haemorrhages and contusion, rotational force is thought to cause deeper level trauma to white matter, leading to diffuse axonal injury (DAI) or axonal shear injury. DAI frequently presents as a diagnostic imaging challenge for clinicians. This may be especially true for mTBI, since CT and MRI scans taken shortly after injury are often normal despite the presence of neurologically-based symptoms such as poor concentration, vision and balance problems, and/or memory deficits. Secondary injury may be caused by ischemia and a cytotoxic biochemical, biomolecular and/or physiological cascade following primary injury at the cellular level. The path to recovery from mTBI may be determined, at least in part, by the severity of secondary injuries. Secondary injuries are non-mechanical and associated symptoms may be delayed in appearance (up to weeks or a month later) when traditional neuroimaging methods are utilized.

While imaging methods such as CT and MRI can be useful in diagnosis of mTBI, the examination equipment is large and expensive and frequently cannot be accessed immediately following an injury (on a sideline or in an operational setting). Examples of tests currently in use for side-line sports-related concussion are neuro-cognitive tests or surveys and include the King-Devick Test, the SCAT-2 test, Immediate Post-Concussion Assessment and Cognitive Testing (ImPACT®) and Post-Concussion Symptom Scale scores (PCSS). Self-reporting is subjective and cognitive tests for concussion can lead to results skewed by players "sandbagging", that is, deliberately performing poorly on pre-trauma baseline testing. Results can also be influenced by other factors such as fatigue. In exemplary embodiments, an objective test (like the test tests described herein) may avoid these risks, eliminate, or at least reduce, the potential for "sandbagging" or malingering, and provide a more reliable metric for whether or not a player is well enough to return to play.

Oculomotor dysfunctions, eye tracking problems, occur commonly in TBI. Approximately 60% of mTBI patients will present with some oculomotor dysfunction and up to 90% of individuals presenting with mTBI injury in a clinical setting are diagnosed with one or more oculomotor dysfunctions during their acute care phase or during recovery. Predictive visual tracking requires attention and working memory both of which are affected in mTBI. Attention and working memory may be associated with the prefrontal cortex, which typically is affected in mTBI injury. Temporal lobe compression that can occur in mTBI can damage the midbrain III nucleus or efferent II nerve and lead to pupil dilation.

Accordingly, a device (such as the device described herein) that is capable of measuring pupil and eye movement responses to stimuli that probe for symptoms of mTBI could replace or supplement existing screening methods, including neurocognitive testing at the injury site, and complement existing diagnostic methods in primary or urgent care settings. The device may provide a clinically useful tool for the diagnosis of mTBI and provide incremental diagnostic information for healthcare providers to consider in their complex decision-making processes for the management of e.g., mTBI.

In exemplary embodiments, the device may be configured to measure any combination of one or more of the following metrics: visual field, contrast sensitivity, color discrimination, distance cover test, strabismus, pupil diameter, constriction velocity, constriction latency, constriction amplitude, dilation velocity, relative afferent papillary defect, gaze stability, saccade amplitude, saccade velocity, saccade latency, saccade accuracy, anti-saccade accuracy, self-paced velocity, pursuit smoothness, predictive saccade latency, pursuit gain, gaze-evoked nystagmus, memory-guided saccade accuracy, near point of convergence in disease, vergence fusional amplitude, and vergence peak velocity. In exemplary embodiments, the combinations of one or more of these metrics may be relevant to mTBI (e.g., concussions) or other pathologies and may be measured by the device described herein.

In general, the device may consist of three main components or subsystems. One subsystem may be responsible for display of stimuli on a display such that the left eye sees only the left side of the screen and the right eye only the right side. Another subsystem may monitor movements of both eyes and the size (e.g., diameter) of one or both pupils. The third subsystem may be a computer/processor and/or software that controls the first two subsystems, analyzes the results, and provides a user interface.

Together, these subsystems in the device may be capable of performing specific testing procedures, as described herein, to identify and diagnose one or more pathologies of an individual.

In exemplary embodiments, the device may be a tabletop device or a portable device.

FIG. 1 is a schematic diagram of an exemplary device for use in measuring eye movement and/or pupil response. Specifically, FIG. 1 illustrates one side of the device—i.e., the portion of the device for a single eye. It should be understood that a second portion of the device, essentially similar to the illustrated portion may be provided for the other eye. As illustrated, the device 100 is configured to allow an individual to look into the device via a window 102. In exemplary embodiments, the device may comprise a nose bridge, a chin rest, or both to assist with proper patient alignment. When the individual looks into the device, the individual looks through a viewing lens 104 and at a display 106. The display 106 may be moved relative to the viewing lens 104 and may also be movable in the vertical direction. As would be understood, the device may include a separate window 102 for each eye or a single window 102 for both eyes. Similarly, the device 100 may comprise a single display for both eyes or individual displays to each eye. In addition, the device 100 may comprise one or more LEDs 108 for illuminating the eye or eyes of the individual. In exemplary embodiments, the LED(s) 108 may be located adjacent to the viewing lens 104. In exemplary embodiments, one or more LEDs may be provided for each eye. In exemplary embodiments, the LEDs may be infrared LEDs.

In exemplary embodiments, the LED(s) may illuminate the individual's eyes and a portion of the light may be reflected from the eyes and onto mirror. In exemplary embodiments, the mirror 110 may be an adjustable mirror 110. The reflected light may then pass through a beam splitter 112 and a portion of the light may be captured by a camera 114. The images captured by the camera may be sent to a computer/processor for analysis. In exemplary embodiments, the adjustable mirror 110 may be driven by a motor (not shown) to rotate the adjustable mirror 110 about a substantially horizontal axis through the center of the adjustable mirror 110. In exemplary embodiments, the motor may be driven by the computer/processor to adjust the image as necessary. For example, the computer may adjust the motor such that the image of the pupil is roughly centered in the camera view. In exemplary embodiments, this may compensate for patients whose eyes are higher or lower with respect to the head support.

Additionally, in exemplary embodiments, the optical system, including e.g., the display, may be driven by another motor (not shown) towards and/or away from the individual, to focus the images of the pupils, as desired.

In exemplary embodiments, the display may be moved relative to the viewing lens to test for e.g., vergence.

In exemplary embodiments, the device may comprise controls to allow the patient to interact with the device.

The device 100 may also comprise a cataract measuring system. In exemplary embodiments, the cataract measuring portion of the device may comprise the beam splitter 112, a cataract LED lens 116, the cataract LED 118, the dichroic mirror 120, and the cataract fixation LED 122 (e.g., a blue LED). In exemplary embodiments, the cataract LED 118 may be a source of infrared light which passes through the dichroic mirror 120 and is collimated by the cataract LED lens 116. Approximately half of that light may reflect from the beam splitter and adjustable mirror and enter the pupil. The optics of the eye form an image of the LED on the retina. In exemplary embodiments, the image of the LED may be slightly defocused if the patient has a refractive error, resulting in an image of the cataract with slightly less contrast of the cataract. Some of the light reflected from the retina may travel back along the input path and a portion (e.g., half) of that may pass through the beam splitter 112 to the camera 114, which then sends an image of the backlit pupil to the computer/processor. During the cataract imaging process, the LEDs 108 may be turned off so that the image of each eye can be analyzed to measure the strength of a cataract.

In exemplary embodiments during the cataract measurement, the individual may be instructed to look downward toward the mirror 110 to look at the LED 122 (blue dot). The individual may be instructed to stare at the LEDs 122 during the few seconds that it takes to collect the images for the cataract measurement.

In exemplary embodiments, the device may have any combination of one or more of the following specifications:

| Feature | Pupil Response | Eye Tracking |
|---|---|---|
| Measurement type | Pupil center and shape | Direction of gaze |
| Monocular sampling rate, typical | about 60 samples per second | about 400 samples per second |
| Binocular sampling rate, typical | about 60 samples per second | about 400 samples per second |
| Minimum pupil diameter | about 2 mm | NA |
| Stimulus field of view | about 30 degrees | |
| Gaze angle accuracy | about 15 minutes of arc | |
| Working distance (first optical element to eye) | about 80 mm | |
| Pupil illumination wavelength | about 850 nm | |
| Stimulus Presentation | | |
| Stimulus presentation method | Organic LED screen | |
| Number of tests | >30 tests available | |
| Measurement duration | Variable, depends on protocol, typ. 1 minutes/test | |
| Patient Alignment | | |
| Patient alignment methods | Nose bridge, chin rest | |

In exemplary embodiments, the device may be capable of a pupil response sampling rate of about 45, 50, 55, 60, 65, 70, 75, or 80 samples per second. In exemplary embodiments, the device may be capable of an eye tracking sampling rate of about 300, 325, 350, 400, 425, 450, 475, or 500 samples per second. In exemplary embodiments, the device may be capable of a stimulus field of view of about 25, 30, or 35 degrees. In exemplary embodiments, the device may have a gaze angle accuracy of about 10, 12, 15, 17, or 20 minutes of arc. In exemplary embodiments, the device may have a working distance of about 60, 65, 70, 75, 80, 85, 90, 95, or 100 mm.

In operation, an operator may input patient specific information and may select one or more tests that the operator would like to perform on the patient. The patient and/or operator may then interact with the device to move the display toward or away from the patient to bring an image on the display into focus. The instrument may then generate the appropriate stimuli corresponding with the selected test or tests and monitor the movement of the eyes and/or the responses of the pupils. In exemplary embodiments, the recorded data may be saved. In exemplary embodiments the device may measure the angular directions of gaze of the eyes, updated, for example, every millisecond and the diameters of the two pupils, updated, for example, 60 times per second. At the end of the testing session, the results may be analyzed and displayed along with a display of the results e.g., in relation to population norms.

In exemplary embodiments, the results may be stored and/or analyzed on a separate computer (e.g., a laptop computer) or a remote server.

In exemplary embodiments, to perform a test, the operator may see the video from the two cameras on a display and may use a mouse to roughly center the image of each pupil on its window (e.g., rotate the adjustable mirror 110 for vertical positioning and move the region of interest of the camera for horizontal and vertical positioning, in software). The operator may then initiate the test In exemplary embodiments, the device may be configured to measure any combination of one or more of pupil shape, anisocoria, gaze angle, constriction velocity, constriction latency, constriction amplitude, amplitude reduction time, dilation velocity, gaze change (saccade) amplitude, gaze change velocity, gaze change latency, gaze change accuracy, gaze change smoothness, gaze change damping, Fourier amplitude of changes in pupil size, inter-eye comparison, compare with normative, compare longitudinal with self.

Exemplary Tests:

In exemplary embodiments, the described device may be capable of performing a plurality of tests. Some of these tests and their usefulness are described herein.

Relative Afferent Pupil Defect (RAPD)—

In an exemplary embodiment of this test, a flash of light may be delivered alternately to the two eyes. For example, each eye may receive about 8 flashes. The flashes can be uniform large disks or annuli and the device may monitor and measure the response of the pupils, e.g. latency of constriction, amplitude, velocity, etc., and the various measurements may be compared between flashes presented to the two eyes. For example, the median latency of the right pupil when the flash is delivered to the right eye may be compared with the median latency of the right pupil when the flash is delivered to the left eye. This measurement, for example, may provide a measure of the relative sensitivities of the left and right retinas.

In exemplary embodiments, the brightness of the flashes delivered to the two eyes may be corrected for differences in pupil area (anisocoria), and any asymmetry in severity of cataracts between the two eyes may be identified and accounted for. Additionally, because glaucoma usually causes arcuately-shaped regions of reduced sensitivity, annuli light flashes may provide more sensitive measures of glaucoma than disk-shaped light flashes.

In exemplary embodiments, some of the parameters that may be measured include, latency, amplitude, time from onset of constriction to maximum constriction, maximum rate of constriction, time constant of reduction in amplitude, and/or rate of redilation. The difference or a weighted combination of differences may be compared between the eyes and/or with normal population data.

In exemplary embodiments, there may be two properties of eyes that can confound measures of RAPD. The first is a condition called "anisocoria", in which the diameters of the pupils of the two eyes differ. The second is the presence of cataracts.

In some patients, if the display delivers the same intensity of flash to both eyes, and if one pupil is larger than the other, than the flash intensity at the retina of the larger eye will be greater than the flash intensity in the other eye, so even if there is not a sensitivity difference between the two retinas, an RAPD may result. The amount of light arriving at a retina from any ordinary display is proportional to the area of the pupil. Therefore, to prevent (or at least reduce) this artifact, in exemplary embodiments, the intensity of the flash presented to each eye may be automatically modified in inverse proportion to the area of the corresponding pupil. (In exemplary embodiments, the area may be measured immediately before each flash is delivered.) In this way, the amount of illumination to the two retinas is constant and independent of pupil size. In exemplary embodiments, compensation for pupil size may be provided. For example, the area of each pupil may be measured before the flash; the intensity of the subsequent flash may then be computed as a "base" intensity divided by the pupil area, the result multiplied by a constant; and the resulting value may be used to control the brightness of the region of the screen to be brightened.

Cataracts are regions in the lens of the eye which scatter and may absorb light. Therefore, if cataractous tissue is present in an eye, it may affect one or both of the amount of light falling on the retina and its spread. Both of those factors may affect the strength of the resulting pupil constriction. As a result, if a patient has cataracts that differ between the two eyes, even if that patient has no difference in retinal sensitivity between the two eyes, a positive RAPD may result. To prevent, or at least reduce the likelihood of this factor contaminating the results of the RAPD test, the strength of cataract may be measured in each eye. If the strengths are equal (or substantially equal), no correction may be necessary. If they are not equal, then, if the RAPD indicates that one retina is significantly less sensitive than the other and if the cataract in the more sensitive eye is stronger than the cataract in the less sensitive eye, then the RAPD indication may be correct (although its strength may not be). If the lesser retinal sensitivity is in the same eye as the greater cataract, then the result may be disregarded.

Relative Efferent Pupillary Defect (REPD)—

In an exemplary embodiment of this test, the test may be similar to the RAPD test but different analyses of the results may be used to measure characteristics of pupil responses to flashes, e.g. maximum velocity of constriction and/or differences between the properties of the responses between the two pupils.

In exemplary embodiments, some of the parameters that may be measured include, latency, amplitude, maximum velocity of constriction, maximum velocity of redilation, and differences between the measures for the two pupils providing the output. The difference or a weighted combination of differences may be compared between the eyes and/or with normal population data.

Hemi-RAPD—

In exemplary embodiments of this test, the RAPD test may be conducted with the flash of light stimulus directed to one hemisphere of one eye, which may include the left and right hemisphere of the left eye and the left and right hemisphere of the right eye. Differences in metrics such as the median latency of response when the flash is delivered to the right hemisphere of the right eye when compared to the median latency of response when the flash is delivered to the right hemisphere of the left eye or when the flash is delivered to the left hemisphere of the right eye may be measured.

Steady Viewing—

In an exemplary embodiment of this test, a stimulus may be presented to either or both eyes as a steady pattern, e.g., a disk, and the pupil diameters may be measured. Under these conditions, pupils typically oscillate slightly in diameter but strong oscillations, called hippus, may indicate pathology. Accordingly, in exemplary embodiments, the test may perform a Fourier analysis of changes in pupil size. In exemplary embodiments, the area under a plot of amplitude vs. frequency, and the frequency of maximum amplitude, may be compared with normative population data.

Selected Light Levels—

In exemplary embodiments of this test, the pupil diameters under various light levels may be measured. In exemplary embodiments, the light levels may represent daylight and dim illumination. In exemplary embodiments, this test may be performed with the steady viewing test. In exemplary embodiments, the test may measure the average pupil diameters, the maximum pupil diameters, the standard pupil diameters, the relative frequency of occurrence of saccades to left vs right, the average oscillation frequency (if oscillation exists), and/or the maximum velocity in smooth and fast phases of nystagmus. In exemplary embodiments, the a standard X-Y plot of gaze angle and/or a standard pupil diameter plot (to look for hippus) may be provided.

Pupil Response to Convergence—

In exemplary embodiments of this test, the same image may be presented to both eyes and the distance between the two patterns on the screen may be set so that the two targets fuse. The screen may be axially positioned to be in the focal plane of the viewing lenses so that it appears to be at infinity. The screen is then smoothly moved toward the patient until it is as close as it can get and then smoothly moved back to its original distance. In a healthy visual system, the result may be a smooth change in diameter of both pupils in proportion to the nearness of the target. (The angles of gaze may also change, as described in connection with Smooth Convergence) A change in pupil diameter without a corresponding change in gaze angle, or a change in gaze angle without corresponding change in diameter, may indicate specific pathology. Accordingly, in exemplary embodiments, this test may measure the slope of the relationship between target optical distance and pupil diameter and compare the results with population norms.

Floppy Iris—

In exemplary embodiments of this test, a target, presented to one or both eyes, jumps from center upwards and then downwards, and the shape of the pupil is visually observed. A floppy iris changes its shape during the eye motion. In connection with this test, the device may be able to provide a useful quantitative measure of change in shape including, e.g. the variance of a measure of how strongly the pupil departs from elliptical during the eye movement.

Pupil Perimetry—

In exemplary embodiments of this test, a small fixation point may be constantly presented at substantially the center of the field of view to one or both eyes. A second small bright spot, at a different location and visible to one eye, is briefly illuminated against a dimly lighted background and the pupil response is recorded. Over a set of trials, the second spot may be presented at different locations. The data are then analyzed and presented in the form of a map showing the amplitude (or latency) of the response at each tested position. In this way, the sensitivities of regions of the retina that drive pupil constriction are mapped. In exemplary embodiments, the amplitude and latency of pupil constriction may be mapped as a function of the position of the stimulus flash. Those measures may be compared with normative data and also with sensitivity maps measured in other ways (e.g., standard perimetry).

Fatigue in Early Glaucoma—

The process of glaucoma kills ganglion cells in the retina. All current glaucoma testing procedures detect manifestations of the loss of functional ganglion cells. However, it seems likely that the early stages of ganglion cell impairment, before they actually cease to function, would involve increases in their refractory period, that is, the time required for a cell to recover its polarization, after firing, to a degree sufficient for it to fire again. Assuming this is the case, then early stages of glaucoma may result in decreases in the maximum firing rate of ganglion cells. Accordingly, in exemplary embodiments of this test, a disk or annular stimulus may be flickered or its intensity may be sinusoidally modulated between a fixed maximum and minimum brightness at a frequency that begins at a low value and smoothly increases, while the diameter or either or both pupils is recorded. Early stages of glaucoma should cause the modulation of pupil diameter to become undetectable at a lower modulation frequency than for a normal eye. In exemplary embodiments, this procedure may be followed with the stimulus delivered to one eye and then repeated with the stimulus delivered to the other eye.

In exemplary embodiments, it may be useful to automatically adjust the brightness (or, in this case, the range of brightnesses) in accordance with the pupil area, so that the retinal illuminance is independent of pupil size. Another method to perform an equivalent measure is to modulate the intensity of the stimulus at a fixed rate and amplitude and measure the decrease in amplitude of pupil response that should occur over time.

In a related procedure, the brightness of the stimulus may be sinusoidally modulated to one eye while sinusoidally modulating the brightness of the stimulus to the other eye at the same frequency and amplitude but with a 180 degree phase shift. Perform this test at a smoothly increasing frequency or decreasing amplitude at fixed frequency and determine the frequency or amplitude at which the pupil responses become undetectable. The same procedure, except modulating the brightness with a square wave may also provide different useful information about glaucoma.

In exemplary embodiments, these tests may measure the amplitude of the change in pupil diameter and compare the results with population norms and/or earlier tests on the same patient.

Segmental Palsy—

Certain neurological disorders may cause the various radial muscles of the iris to constrict unequally, causing the pupil to become irregular in shape during constriction. This can be observed visually during any of the other forms of pupil test and can be quantified as a departure from ellipticity.

Anisocoria—

In exemplary embodiments, this test measures the difference between the pupil diameters of the left and right eyes and may be performed under a bright and a dim stimulus level.

Quadrant Stimulation—

In exemplary embodiments, this test may be used to measure relative sensitivities of the different quadrants of field of view in each eye. In the test, for example, the device may flash to illuminate, for example, the superior nasal quadrant in the left eye, then the superior temporal quadrant in the right eye, then the inferior etc. In exemplary embodiments, the test may measure amplitude, latency, etc. of pupil constriction to each flash and compare the measured amplitudes. This compares retinal sensitivities and optic nerve integrity in each quadrant but also post-chiasm, that is, optic tract integrity. For example, if the nasal side of the right eye and the temporal side of the left eye are both less sensitive than the opposite sides, that may indicate a lesion in one optic tract.

Inter-Pupillary Distance—

In exemplary embodiments, this test measures the distance between the centers of the individual's pupils.

Saccadic Clock—

In exemplary embodiments, this test may present a target to one or both eyes. The target may first be presented straight ahead, that is, at the center of the field of view. The target pauses two seconds, then instantly jumps to a new position about 12 degrees away from the center at one of eight positions (e.g. horizontally, or 45 degree up and to the left, etc.) while the directions of gaze of both eyes are recorded. After two seconds, the target returns to the center, pauses two seconds, then jumps to another 12 degree position, etc, until all eight peripheral positions have been tested. Various properties of the movements of the two eyes (e.g. latency, amplitude, directional accuracy, velocity, etc.) are measured. These measures are compared with population norms and also between the two eyes.

In exemplary embodiments, the test may measure, for each eye in each direction, the latency, accuracy (in amplitude and direction), maximum velocity, and damping (that is, the brief under- or over-shoot at the end of each saccade) and compare the corresponding measures between the two eyes and also against population norms. Also, when the target is present to only one eye, the test may measure the rate of drift and final amplitude of the difference in gaze angle between the two eyes (a measure of phoria).

Figure 4:
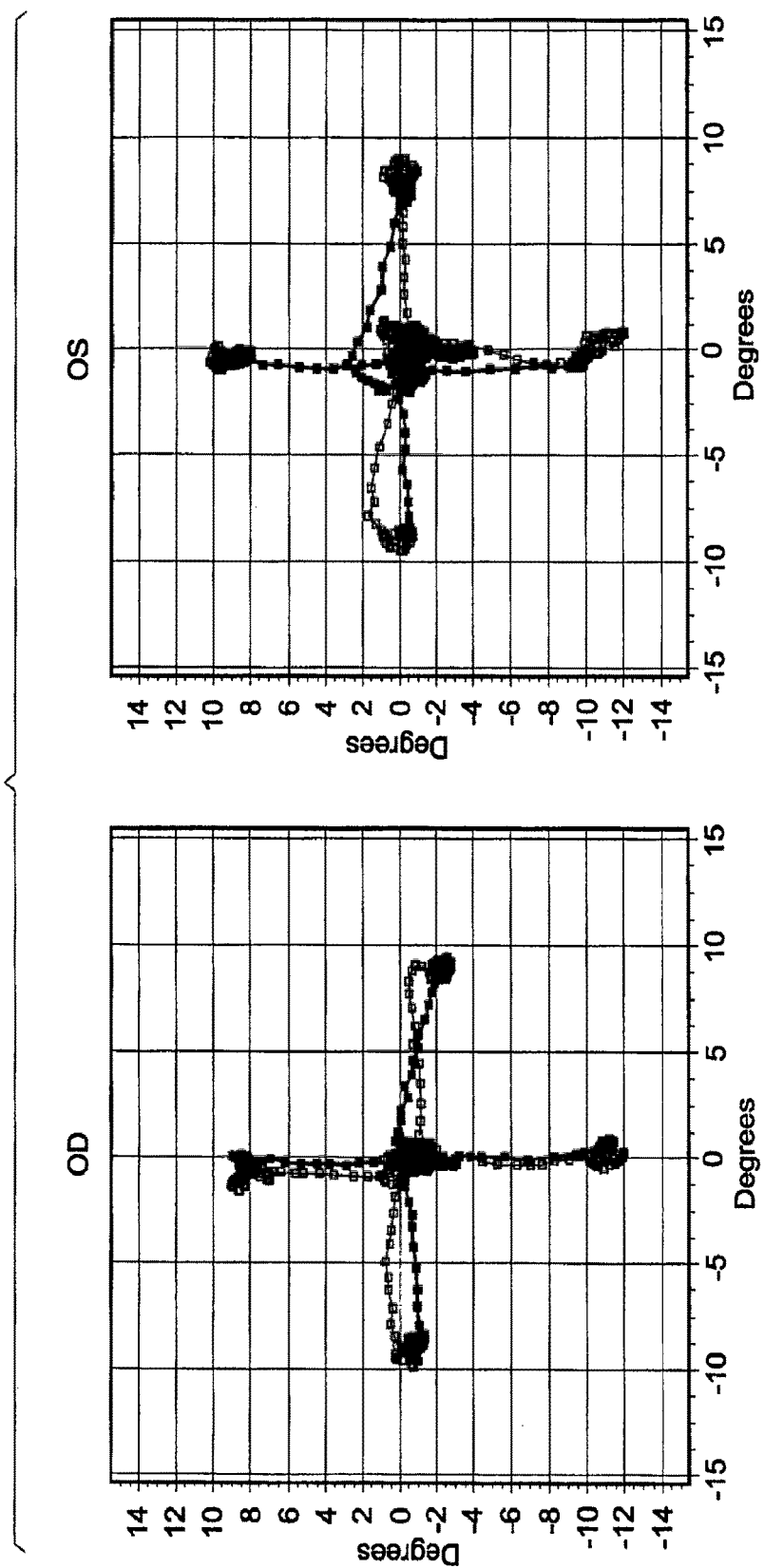
FIG. 4 is an exemplary depiction of results from a saccadic clock test for a healthy patient in which the stimulus is presented at a central fixation point and then at four equally spaced clock hours from the center of the clock with a return to the central point between clock hours.
Figure 5:
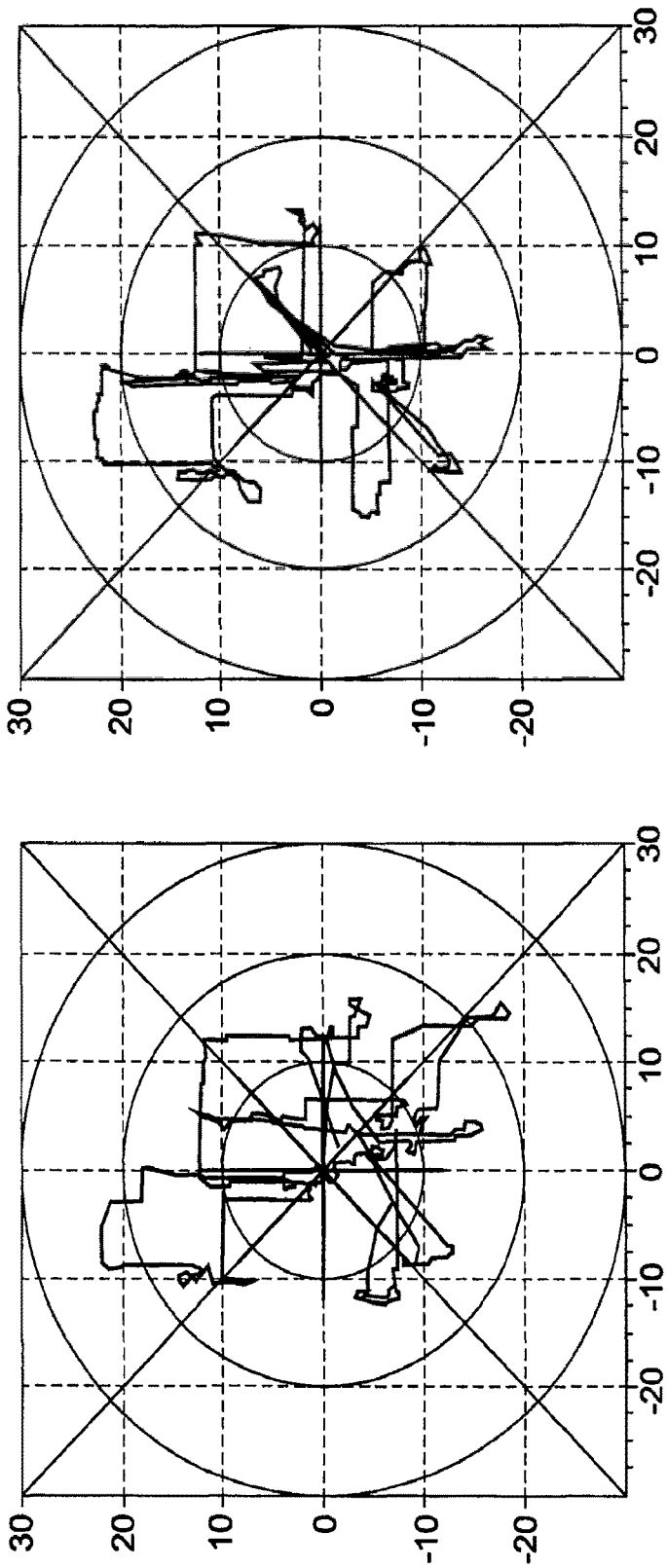
FIG. 5 is an exemplary depiction of results from a saccadic clock test for a diseased patient.

FIG. 4 and FIG. 5 are exemplary depictions of results of the saccadic clock test. The test presents a stimulus first at a central fixation point and then at four equally spaced clock hours at a 12 degree radius from the center of the clock with a return to the central point between clock hours. This test can be used to evaluate a number of issues with ocular motility and neural function by measuring saccadic accuracy, amplitude, velocity, latency, and duration. FIG. 4 is a Saccadic Clock result from a normal patient with no history of disease. FIG. 5 is the same test run on a patient with a disease.

Main Sequence—

In a healthy visual system, the relationship between the velocity of a saccadic eye movement and its amplitude may be a monotonic function with parameters fixed within fairly narrow limits. This relationship has been labeled the "Main Sequence." To measure this in a patient, in exemplary embodiments, the target may abruptly jump from the center out to various distances and back, the resulting velocities and amplitudes are measured and plotted, and the parameters of the relationship are determined and compared with normal data. This test can be performed separately for horizontally and for vertically jumping targets. In exemplary embodiments, amplitude and maximum velocity of saccadic movements may be measured.

Central Fixation with Distraction—

In exemplary embodiments of this test, a fixation target may appear (to either or both eyes) straight ahead. Another target (herein referred to as the "distractor target") may appear somewhere else in the field of view for a short period. The distractor target may disappear and subsequently reappear elsewhere in the field of the same or contralateral eye. The patient may be asked to continue looking at the location of the fixation target (straight ahead) and failure to inhibit eye movements to the distractor target may indicate pathology.

Pulse Test—

In exemplary embodiments of this test, the target may appear as a flash in one eye, followed by a pause, followed by a flash in the other eye, followed by a pause. This process may be repeated multiple times and the results may be evaluated individually or the results may be aggregated via processing such as the mean or median to return a single set of data for evaluation. The ipsilateral and contralateral constriction and subsequent dilation latencies, amplitudes, and velocities may be measured for both eyes. The difference in these metrics between the eyes, in one eye against a baseline measurement on the same eye, or for one eye or the difference between eyes against a baseline normative data set may be indicative of disease.

Figure 3:
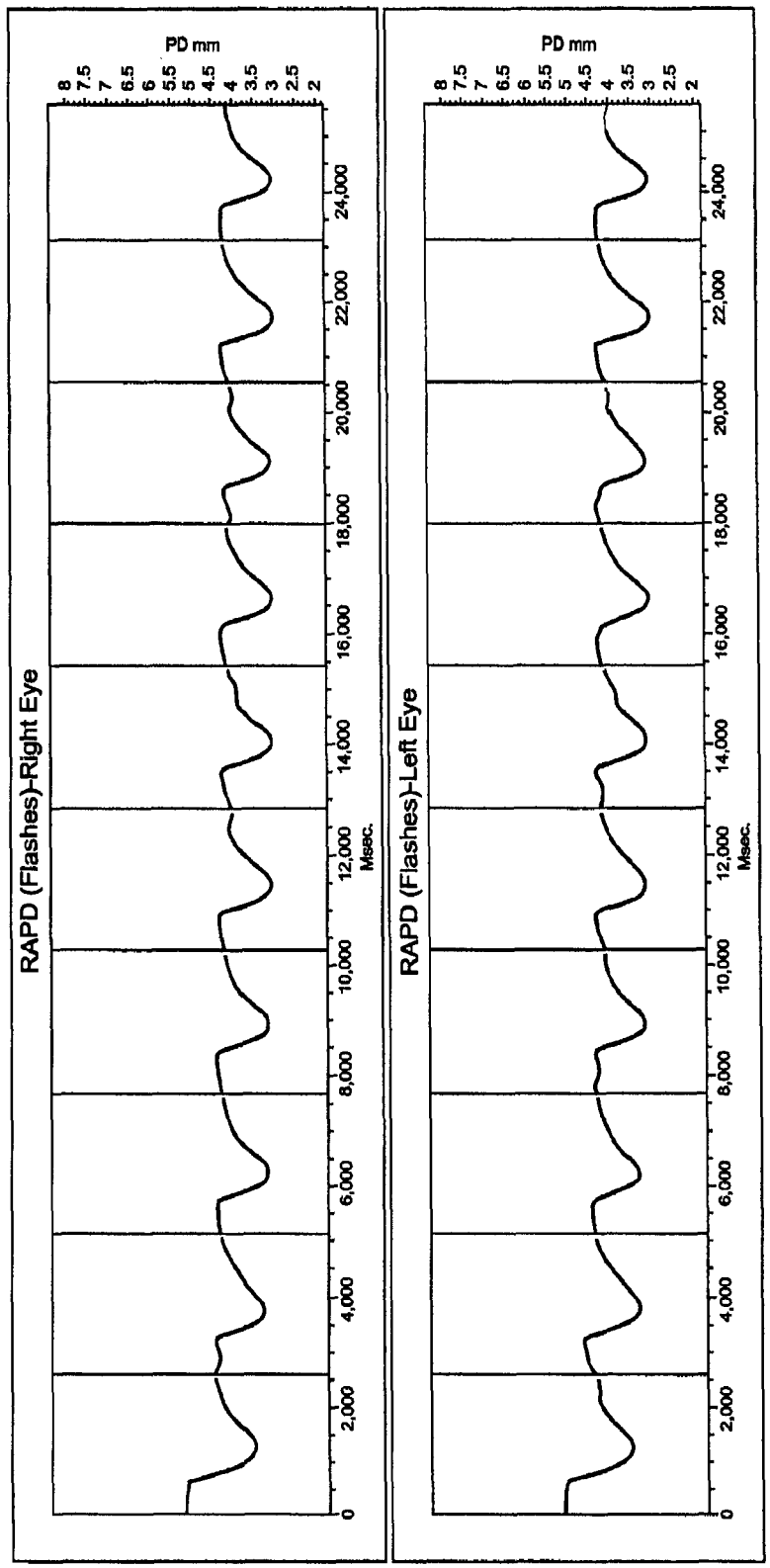
FIG. 3 is an exemplary depiction of results from a pulse test in which the stimulus is a flash of light that is presented to one eye and then the other and pupil response is measured for both eyes.

FIG. 3 is an exemplary depiction of results from a pulse test. The plot indicates the pupil diameter as a function of time in both the left and right pupils. Differences in pupil response, including constriction or dilation velocity, amplitude, or duration, between the eyes or changes in pupil response relative to a baseline measurement on the same patient or normative data could indicate disease state.

Blanked Delay ("Inhibit")—

In exemplary embodiments of this test, a target may appear (to either or both eyes) straight ahead. The target is extinguished for a short period (e.g., one or two or three seconds) and then suddenly appears at a new location. The patient is asked to continue looking at the location of the original target (straight ahead) until the new one appears. Failure to delay the eye movement may indicate pathology.

Overlap—

In exemplary embodiments, this test may provide a target image which appears in front of the individual for about two seconds. Than a second target appears (in addition to the first one) at a new location. The patient may be instructed to look at the first target until the second one appears and then to look at the second one as quickly as possible. A long latency in looking at the second target may indicate pathology.

Remembered—

In exemplary embodiments of this test, the target may appear straight ahead, jumps to a new position, then jumps back. The patient is instructed to wait until the target has returned to the center and then to look at where the target had previously been. Failure to look to the correct position may indicate pathology.

Opposite—

In exemplary embodiments of this test, the target may jump from the center to a different position and the patient is instructed that when the target jumps away from the center, the patient is to look to the corresponding position in the opposite direction. In exemplary embodiments, the test may measure the direction and amplitude of the first saccade after the jump, in relation to the direction and amplitude of the jump.

Self-Paced—

In exemplary embodiments of this test, two targets may be presented one to the left of center and the other to the right. The patient is asked to look back and forth between the two targets as fast as he or she can. An abnormally low frequency of shifting may indicate pathology. Accordingly, in exemplary embodiments, the test may measure how many approximately correct saccades occur per unit time Brief Remembered—

In exemplary embodiments of this test, two targets, one to the left and the other to the right of center, are simultaneously and briefly presented (<100 msec) and the patient is asked to look first at the location where one had been and then at the location where the other had been. Abnormal accuracy may indicate pathology.

Memory—

In exemplary embodiments of this test, the fixation target may appear straight ahead, while small targets (herein referred to as "memory targets") may appear for a fixed amount of time at a location away from the fixation target and then disappear. These targets may appear in serial order with memory target 1 appearing and then disappearing, and then memory target 2 appearing in a different location, and so on. The fixation target may disappear after the last memory target has disappeared. The patient may then be instructed to look to the locations where the memory targets had been when the fixation target disappears. Failure to look to the correct position or positions (herein referred to as "memory saccade position error") may indicate pathology.

Withhold Response—

In exemplary embodiments of this test, the target may be initially centered and then suddenly jump to a new position. The patient is instructed to continue looking at the original position until a tone is sounded, and then to look at the new position. Inability to inhibit the movement until the tone may indicate pathology. In exemplary embodiments, the test may measure the frequency of occurrence of saccade before the tone.

Smooth Spiral—

In exemplary embodiments of this test, a target is presented to either or both eyes and may be initially centered. The target then moves with a constant (or substantially constant) speed in an outward spiral. The patient is instructed to follow the target. The accuracy and smoothness of the tracking (lack of saccadic movements) is evaluated and the relationship between responses of the two eyes is also evaluated. In exemplary embodiments, the following measurements may be made: mean error of fixation, number of saccades, mean difference in gaze angle between the two eyes.

Figure 2:
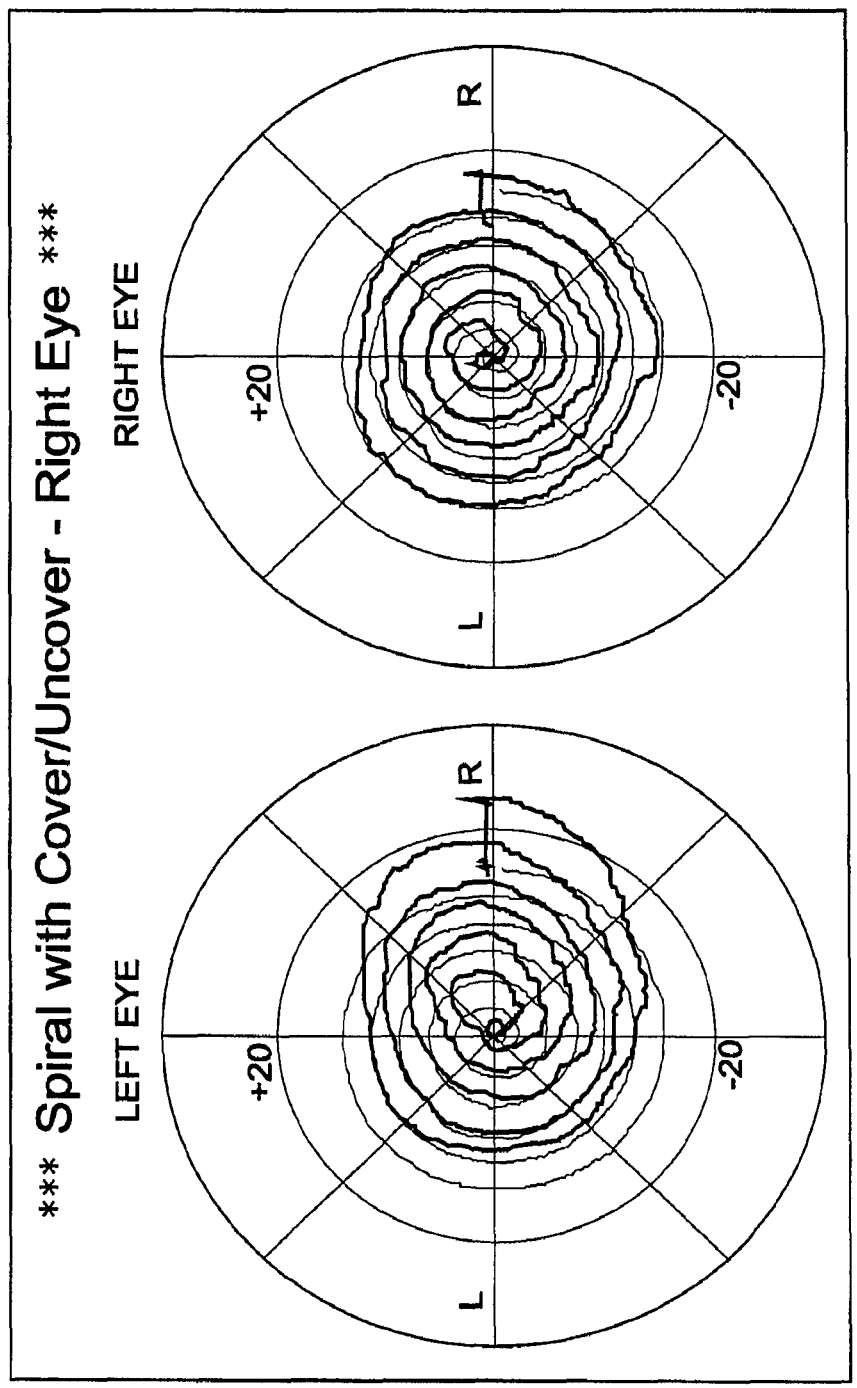
FIG. 2 is an exemplary depiction of results from a spiral test in which a stimulus point moves outward with a spiral motion from the center of the display.

FIG. 2 is an exemplary depiction of results from a spiral test in which a stimulus point moves outward with a spiral motion from the center of the display. The radial plot indicates gaze angle and stimulus angle over the course of the test. This test evaluates smooth pursuit and prediction, and accuracy errors (large deviations in gaze angle from the actual target position) or high tracking lag (gaze angle on average lags behind the target position by a large amount) relative to a baseline measurement on the same patient or normative data could indicate disease.

Accelerating Circle—

In exemplary embodiments of this test, the target may move in a circular path with an accelerating speed. The speed at which smooth following fails (breaks into saccades) may be measured and compared with norms.

Accelerating Circle with Distraction—

In exemplary embodiments of this test, the target may move in a circular path with an accelerating (or merely changing) speed. During pursuit, additional targets may be presented in eccentric locations within the field of view. The speed at which smooth following fails (breaks into saccades) may be measured and compared with norms. The smooth pursuit error is the deviation of measured gaze angle and position relative to known Accelerating Circle target angle. Increased smooth pursuit error relative to a baseline or normative data may be measured.

Sinusoidal—

In exemplary embodiments of this test, the target may move horizontally or vertically in a sinusoidal motion with increasing frequency. The frequency at which smooth tracking fails may be measured.

Saw-Tooth—

In exemplary embodiments of this test, the target may move horizontally or vertically in a saw-tooth path with increasing frequency. The velocity at which smooth tracking breaks down (saccades occur) and/or presence or absence of smooth reversal in direction at reversals in stimulus direction may be measured.

Convergence—

In exemplary embodiments of this test, the target may be initially presented to both eyes at optical infinity and move smoothly toward, then away from the patient. The directions of gaze of the two eyes may be measured and a mean error in direction of gaze of each eye and/or closest distance for which smooth convergence occurs may also be measured AMD Demonstration or Simulation—

Patients with macular degeneration lose central vision. This loss can be much more devastating than a sighted person can imagine. The AMD demonstration is not a test per se, but rather a way of demonstrating, for example to the spouse of a person with AMD, how debilitating the condition can be. In exemplary embodiments, a scene or some text is presented on the screen, to either eye, but a small region of the display substantially centered where the viewer is looking is missing. That is, the content of the region being fixated at each moment is replaced by a region of uniform brightness, the same brightness as the background of the scene. The viewer therefore sees what an AMD patient sees.

Phorias and Tropias—

When a patient with a healthy visual system looks at a target with both eyes, the directions of gaze of the two eyes coincide at the target. If they do not, the patient is said to have a tropia. If they do coincide but when one eye is blocked from seeing the target, that eye drifts away from its previous direction, the patient is said to have a phoria. The classical methods for detecting phorias and tropias involve watching the patient's eyes when neither eye is blocked, then when first one and then the other is blocked. These tests are called the "cover" and the "cover-uncover" test. To quantify the degree of phoria or tropia, the examiner performs the test while placing prisms of various powers in front of the unblocked eye. In exemplary embodiments described herein, the tests may be performed as described below. A target (e.g., an image) may initially be visible to both eyes, and the directions of gaze of both eyes may be continuously recorded. After a few seconds, the target disappears from one eye, after a few more, the target reappears to both eyes, then the target is blocked from the second eye, and finally the target is again visible to both eyes. If, when the target disappears to one eye, that eye drifts smoothly outward, the patient is said to have an exophoria. If the blocked eye drifts inward, the patient has an esophoria. The eye eventually stops drifting, and the distance through which it drifted (computed as a change in the angle of gaze) may be a measure of the degree of the phoria.

If, when the target disappears to one eye and there is no saccadic change in gaze angle of that eye but when the other eye is blocked, there is a saccadic movement (of both eyes), the patient has a tropia, and the amplitude of the saccade may be a measure of the degree of the tropia. A tropia that has been present for only a short time may cause the patient to see double under normal viewing conditions (diplopia), but eventually, if the patient has a tropia, vision from one eye will be suppressed and the function of that eye may worsen. During the tropia test, the eye which, when blocked, elicits a saccadic eye movement, is the dominant, unsuppressed eye. Detecting and measuring phorias and tropias may be an important part of any ophthalmic or optometric examination. Phorias and tropias can be corrected by introducing prismatic power into spectacle lenses. If not corrected, phorias may cause headaches and tropias may reduce cues for seeing depth.

Malingering (Drifting Grating)—

In exemplary embodiments of this test, a grating, consisting of vertical lines, may drift horizontally across the display, while the patient's eye movements are recorded. If the patient can see the grating, the eyes will move in a characteristic way, making a series of smooth movements in the direction of motion of the grating and small saccadic movements in the opposite direction. A patient who can see the stripes but claims he or she is blind cannot avoid making such eye movements.

Smooth movements in the direction of grating movement among saccades in the opposite direction are called Optokinetic Nystagmus (OKN). Differences in OKN between right and left-moving gratings may indicate pathology.

This same test, but performed with finer and finer gratings, may provide a measure of visual acuity for patients who cannot communicate well with the examiner.

Nystagmus—

In exemplary embodiments of this test, during steady viewing of a stationary target, the movements of both eyes may be measured. The presence of repeated smooth movements in one direction and saccadic movements in the opposite direction may indicate pathology. Accordingly, in exemplary embodiments, the relative frequency of occurrence and amplitude of saccades to left vs right or up vs. down may be identified.

Exemplary Pathologies:

In exemplary embodiments, the described device may be capable of performing a combination of one or more of the above-described tests to diagnose a particular pathology. In exemplary embodiments, the order of the tests may be fixed or randomized. Some of the pathologies and associated tests are described herein.

Concussion and Mild Traumatic Brain Injury

Concussive symptoms may be broken into acute (immediately after injury) and chronic (greater than 24 hours after injury) symptoms. In general, some symptoms of concussions include deficits in working memory, attention, balance, and coordination. Concussion may be considered a form of mild Traumatic Brain Injury (mTBI) and Post-Concussion Syndrome (PCS) is a set of symptoms that persists after the concussion injury.

Post-concussive syndrome is associated with diffuse axonal injury (DAI) as part of an injury. MRI and Diffuse Tensor Imaging as well as neurophysiological testing (which may include subjective surveys (e.g., ImPACT), reflex, and balance tests) are currently used to identify patients which may be suffering from concussions.

In exemplary embodiments, test results from one or more of the tests described throughout this specification may indicate the presence of mTBI. The results of these tests may be compared to a baseline data set acquired on the same patient (herein referred to as the "baseline") and/or may be compared to the aggregate results of a control group (herein referred to as "normative data").

For example, in exemplary embodiments, the Accelerating Circle Test may be utilized. In exemplary embodiments of this test, the target may move in a circular path with an accelerating speed. The speed at which smooth following fails (breaks into saccades) may be measured and compared with norms. The smooth pursuit error is the deviation of measured gaze angle and location relative to known Accelerating Circle target angle and location. Increased smooth pursuit error relative to a baseline or normative data may be measured.

In exemplary embodiments, the following test results may indicate the presence of mTBI:
(1) Smooth Pursuit Breakdown Speed—the velocity at which smooth pursuit breaks into saccades may be different (e.g., lower) in concussion relative to the baseline or normative data;
(2) Smooth Pursuit Error—the smooth pursuit error may be different (e.g., higher) in concussion relative to the baseline or normative data.

In exemplary embodiments, the Accelerating Circle with Distraction Test (described elsewhere herein) may also be utilized to identify the presence of concussion.

In exemplary embodiments, the following test results may indicate the presence of mTBI:
(1) Smooth Pursuit Breakdown Speed—the velocity at which smooth pursuit breaks into saccades may be lower in concussion relative to the baseline or normative data;
(2) Smooth Pursuit Error—the smooth pursuit error may be different (e.g., higher) in concussion relative to the baseline or normative data;
(3) In the presence of a distraction, the smooth pursuit error may be more pronounced in concussion relative to the baseline or normative data.

In exemplary embodiments, the Sinusoudal Test (described elsewhere herein) may also be utilized. In exemplary embodiments, the following test results may indicate the presence of mTBI:
(1) Pursuit Speed—the maximum velocity may be lower and the velocity error may be different (e.g., higher) in concussion relative to the baseline or normative data;
(2) Pursuit Lag—the average phase lag between the actual gaze angle and the gaze angle expected given the known target position during the trial may be different (e.g., higher) in concussion relative to the baseline or normative data.

In exemplary embodiments, the Sawtooth Test (described elsewhere herein) may also be utilized. In exemplary embodiments, the following test results may indicate the presence of mTBI:
(1) Smooth Pursuit Breakdown Speed—the velocity at which smooth pursuit breaks into saccades may be different (e.g., lower) in concussion relative to the baseline or normative data;
(2) Smooth Direction Reversals—the presence of smooth direction reversals may be different in concussion relative to the baseline or normative data.

In exemplary embodiments, the Pulse Test (described elsewhere herein) may also be utilized.

In exemplary embodiments, the following test results may indicate the presence of mTBI:
(1) Any deviation in the ipsilateral or contralateral constriction and subsequent dilation latencies, amplitudes, and velocities or derived metrics, such as relative difference in constriction velocity between the two eyes while one eye is stimulated, may be different in concussion relative to the baseline or normative data.

In exemplary embodiments, the Hemi-RAPD Test (described elsewhere herein) may also be utilized.

In exemplary embodiments, the following test results may indicate the presence of mTBI:
(1) Any deviation in the measured pupil response values such as latency of constriction or amplitude, or metrics derived thereof, may be different in concussion relative to the baseline or normative data.

In exemplary embodiments, the Saccadic Clock Test (described elsewhere herein) may also be utilized. In exemplary embodiments, the following test results may indicate the presence of mTBI:
(1) Any deviation in the saccade accuracy, latency, velocity, or derived metrics, such as relative difference in speed between clock angles between the two eyes, may be different in concussion relative to the baseline or normative data.

In exemplary embodiments, Central Fixation with Distraction Test (described elsewhere herein) may also be utilized.

In exemplary embodiments, the following test results may indicate the presence of mTBI:
(1) Saccade Error—the number of saccades to the position of the distracting target may be different (e.g., higher) in concussion relative to the baseline or normative data.

In exemplary embodiments, the Opposite Test (described elsewhere herein) may also be utilized. In exemplary embodiments, the following test results may indicate the presence of mTBI:
(1) Saccade Acceleration—the time to peak saccade speed for anti-saccades may be different (e.g., higher) in concussion relative to the baseline or normative data;
(2) Saccade Accuracy—the anti-saccade accuracy may be different (e.g., lower) in concussion relative to the baseline or normative data;
(3) Saccade Duration—the saccade duration may be different (e.g., higher) in concussion relative to the baseline or normative data;
(4) Saccade Latency—the saccade latency may be different (e.g., higher) in concussion relative to the baseline or normative data.

In exemplary embodiments, the Memory Test (described elsewhere herein) may also be utilized.

In exemplary embodiments, the following test results may indicate the presence of mTBI:
(1) Saccade Number—the total number of saccades in the memory task with more than 1 memory target location may be different (e.g., higher) in concussion relative to the baseline or normative data;

(2) Saccade Duration—the average saccade duration over all saccades in the task may be different (e.g., higher) in concussion relative to the baseline or normative data;

(3) Saccade Position—the memory saccade position error may be different (e.g., higher) in concussion relative to the baseline or normative data.

In exemplary embodiments, the Self-Paced Saccades Test (described elsewhere herein) may also be utilized. In exemplary embodiments, the following test results may indicate the presence of mTBI:

(1) Saccade Velocity—the peak saccade velocity may be different (e.g., lower) and time to peak velocity may be longer in concussion relative to the baseline or normative data;

(2) Inter-Saccade Interval—the mean inter-saccade interval may be higher in concussion relative to the baseline or normative data.

In exemplary embodiments, the Pupil Response to Convergence Test (described elsewhere herein) may also be utilized. In exemplary embodiments, the following test results may indicate the presence of mTBI:

(1) Gaze Angle—the mean error in gaze angle may be different (e.g., higher) in concussion relative to the baseline or normative data;

(2) Convergence Distance—the closest distance for which smooth convergence occurs may be different in concussion relative to the baseline or normative data.

In exemplary embodiments, an 11-test mTBI test panel may be defined based on the signs of visual dysfunction associated with mTBI. The table below shows the primary and secondary tests used to probe the measures of visual dysfunction. In exemplary embodiments, the secondary tests may be provided to supplement the information gathered in the primary test. In exemplary embodiments, the 11 tests may be performed independently.

Parkinson's Disease and Parkinsonian Disorders

Parkinson Disease (PD) and Parkinson Disease with Dementia (PDD) symptoms may include difficulty in self-initiation of movements, decreased cortical potential during anticipation of an upcoming stimulus that triggers movement, decreased performance in anti-saccade trials, mild hypometria (undershooting intended position) of upwards voluntary saccades, and/or mildly impaired smooth pursuit. Progressive Supranuclear Palsy (PSP) also characterized by severe saccadic hypometria, slow saccades, moderate square wave jerks, impaired vestibulo-ocular response, moderately impaired optokinetric response is a further symptom of Parkinson Disease. Corticobasal Syndrome (CBS) characterized by increased smooth pursuit and optokinetic nystagmus errors, increased saccadic hypometria, and apraxia (increased latency) of saccades is a further symptom of Parkinson Disease. Multiple System Atrophy (MSA) characterized by moderate square wave jerks, impaired vestibulo-ocular reflex suppression, moderately impaired optokinetic response, mildly or moderately impaired smooth pursuit and optokinetic response, moderate saccadic hypometria, gaze-evoked nystagmus, positional downbeat nystagmus, and perverted head-shaking nystagmus is another symptom of Parkinson disease.

Parkinson disease involves the death of dopamine-generating cells, which causes a set of issues affecting areas including the motor and oculo-motor pathways. PET, Diffusion MRI, and SPECT are generally used alongside a standard neurological exam to diagnose the particular disease. Diseases in the Parkinsonian family have similar pathologies but can be difficult to differentiate and typically require a differential diagnosis including 1 or more symptoms unique to the disease as well as 1 or more shared symptoms.

| Primary Test | Secondary Test | Analysis Metrics |
| --- | --- | --- |
| Cover, Cover/Uncover | Saccadic Clock | Gaze angle, horizontal |
| Cover, Cover/Uncover | Saccadic Clock | Gaze angle, vertical |
| Pupillary Light Response | Cover, Cover/Uncover | Pupil diameter, pre-stimulus, max |
| Pupillary Light Response | Cover, Cover/Uncover | Pupil diameter, post-stimulus, max |
| Pupillary Light Response | Cover, Cover/Uncover | Pupil ellipticity |
| Pupillary Light Response | Cover, Cover/Uncover | Pupil shape, floppy iris metric |
| Pupillary Light Response | Cover, Cover/Uncover | Pupil diameter, max constriction velocity, max |
| Pupillary Light Response | Cover, Cover/Uncover | Pupil constriction velocity, max |
| Pupillary Light Response | Cover, Cover/Uncover | Pupil constriction latency |
| Pupillary Light Response | Cover, Cover/Uncover | Pupil dilation velocity, max |
| Pupillary Light Response | Cover, Cover/Uncover | Pupil dilation latency |
| Pupillary Light Response | Cover, Cover/Uncover | Pupil diameter, post-dilation, max |
| Pupillary Light Response | Cover, Cover/Uncover | Pupil, RAPD score |
| Pupillary Light Response | Cover, Cover/Uncover | Pupil, REPD score |
| Saccadic Clock | Anti-Saccade | Saccade, start time |
| Saccadic Clock | Anti-Saccade | Saccade, end time |
| Saccadic Clock | Anti-Saccade | Saccade velocity, max |
| Saccadic Clock | Anti-Saccade | Saccade amplitude, max |
| Saccadic Clock | Anti-Saccade | Saccade latency |
| Saccadic Clock | Anti-Saccade | Saccade accuracy |
| Saccadic Clock | Anti-Saccade | Saccade, number of damping saccades |
| Self-Paced | N/A | Saccade, self-paced count |
| Self-Paced | N/A | Saccade, self-paced frequency, max |
| Anti-Saccade | Distractions | Saccade, pro-saccade error count |
| Anti-Saccade | N/A | Saccade, anti-saccade accuracy |
| Working Memory | Delayed Response | Saccade, memory error rate |
| Saccadic Clock | Cover, Cover/Uncover | Saccade, nystagmus frequency |
| Accelerating Circle | Sawtooth | Smooth pursuit accuracy, mean |
| Accelerating Circle | Sawtooth | Smooth pursuit velocity, standard deviation |
| Accelerating Circle | Sawtooth | Smooth pursuit gain, mean |
| Accelerating Circle | Sawtooth | Smooth pursuit error |
| Accelerating Circle | N/A | Smooth pursuit breakdown speed |
| Vergence | N/A | Vergence, fusional amplitude, max |
| Vergence | N/A | Vergence, fusional velocity, max |
| Vergence | N/A | Vergence, fusion break distance |

Test results from one or more of the tests described throughout this specification may indicate the presence of a disease of the Parkinsonian family. The results of these tests may be compared to a baseline data set acquired on the same patient (herein referred to as the "baseline") or may be compared to the aggregate results of a control group (herein referred to as "normative data").

For example, in exemplary embodiments, the Nystagmus Test (described elsewhere herein) may also be utilized. In exemplary embodiments, the following test results may indicate the presence of a disease in the Parkinsonian disease family:
(1) When viewing a stationary target, the direction of gaze may alternately move smoothly in one direction for a fraction of a second and jerk (saccade) in the opposite direction in a manner sometimes known as square wave jerk, the presence of which may indicate PSP or MSA but is not likely to be found in the baseline or normative data.

In exemplary embodiments, the Saccadic Clock Test (described elsewhere herein) may also be utilized. In exemplary embodiments, the following test results may indicate the presence of a disease in the Parkinsonian disease family:
(1) Saccade Accuracy—the presence of hypometria (undershooting the target position) may be more regular in the Parkinsonian disease family relative to the baseline or normative data;
(2) The Parkinsonian disease family (e.g., PSP) also may be characterized by the presence of glissade refixation saccades (a series of small saccades in the same direction) after hypometria more often relative to the baseline or normative data;
(3) The Parkinsonian disease family also may be characterized by upward or downward palsy (reduction of amplitude of movement) relative to the baseline or normative data;
(4) The Parkinsonian disease family (e.g., MSA) may be characterized by the presence of positional (downbeat) nystagmus and rebound (gaze-evoked) nystagmus, both of which are less likely to be found in the baseline or normative data;
(5) Saccade Velocity—the saccade velocity in the upward or downward directions may be different (e.g., lower) in Parkinsonian disease family (e.g., PSP with Richardson Syndrome) relative to the baseline or normative data;
(6) Saccade Latency—the saccade latency may be different (e.g., higher) in the Parkinsonian disease family relative to the baseline or normative data.

In exemplary embodiments, the Accelerating Circle Test (described elsewhere herein) may also be utilized. In exemplary embodiments, the following test results may indicate the presence of a disease in the Parkinsonian disease family:
(1) Smooth Pursuit Breakdown Speed—the velocity at which smooth pursuit breaks into saccades may be different (e.g., lower) may be lower in the Parkinsonian disease family (e.g., PD, PDD, CBS, PSP, MSA) relative to the baseline or normative data;
(2) Smooth Pursuit Error—the smooth pursuit error may be different (e.g., higher) in the Parkinsonian disease family (e.g., PD, PDD, CBS, PSP, MSA) relative to the baseline or normative data.

In exemplary embodiments, the Optokinetic Response Test (described elsewhere herein (see, e.g., Malingering (Drifting Grating)) may also be utilized. In exemplary embodiments, the following test results may indicate the presence of a disease in the Parkinsonian disease family:
(1) Gaze Angle—the reflexive saccades characteristic to the optokinetic response may be different or nonexistent in the Parkinsonian disease family relative to the baseline or normative data.

Glaucoma

Glaucoma is sometimes associated with a decrease in visual field, typically starting as a regional loss of visual field before more pronounced global loss of vision. Glaucoma may affect one or both eyes. Glaucoma is associated with a thinning of the nerve fiber layer, and in some cases may be associated with a higher intra-ocular pressure relative to the baseline or normative data. Glaucoma may be diagnosed through measurements of intraocular pressure, visual field measurements, observation or measurement of the three-dimensional shape of the optic nerve head, and retinal nerve fiber layer thickness measurements.

Test results from one or more of the tests described herein may indicate the presence of glaucoma or other disease affecting the sensitivity of the retina. The results of these tests may be compared to a baseline data set acquired on the same patient (herein referred to as the "baseline") or may be compared to the aggregate results of a control group (herein referred to as "normative data").

For example, in exemplary embodiments, the RAPD Test (described elsewhere herein) may be utilized. In exemplary embodiments, the following test results may indicate the presence of glaucoma:
(1) Relative Difference in Pupil Metrics—the relative difference in pupil response metrics, such as pupil constriction velocity and amplitude, between responses when the flash is delivered to the right eye as compared when the flash is delivered to the left eye of the same subject may be different in glaucoma relative to the baseline or normative data.

In exemplary embodiments, the Fatigue Test (described elsewhere herein) may also be utilized. In exemplary embodiments, the following test results may indicate the presence of glaucoma:
(1) The highest stimulus frequency at which the pupil response is no longer measurable may be different in Glaucoma relative the baseline or normative data.

In exemplary embodiments, the Fatigue Test for Each Eye Separately may also be utilized. In exemplary embodiments, the following test results may indicate the presence of glaucoma:
(1) A difference between the two eyes in the highest frequency for which the pupil response is no longer measurable may indicate glaucoma.

Alzheimer Disease

Alzheimer Disease (AD) is a neuro-degenerative disorder that progressively worsens over time. AD is associated with dementia and loss of memory, among other neurological and psychological symptoms. AD is characterized by changes in the brain that affect memory, attention, and motor inhibition. Alzheimer's disease may be diagnosed through a series of physical wellness and cognitive testing.

Test results from one or more of the tests described throughout this specification may indicate the presence of Alzheimer Disease or a similar neurodegenerative disease. The results of these tests may be compared to a baseline data set acquired on the same patient (herein referred to as the "baseline") or may be compared to the aggregate results of a control group (herein referred to as "normative data").

For example, in exemplary embodiments, the Nystagmus Test (described elsewhere herein) may be utilized. In exemplary embodiments, the following test results may indicate the presence of Alzheimer disease:

(1) Gaze Angle Stability—gaze angle may be more unstable in AD during central fixation relative to the baseline or normative data.

In exemplary embodiments, the Blanked Delay Test (described elsewhere herein) may be utilized. In exemplary embodiments, the following test results may indicate the presence of Alzheimer disease:
(1) Saccade Errors—the number of saccade errors (saccades to the new target location rather than fixated at the first target location) may be higher in AD relative to the baseline or normative data.

In exemplary embodiments, the Opposite test (described elsewhere herein) may be utilized. In exemplary embodiments, the following test results may indicate the presence of Alzheimer disease:
(1) Reflexive Saccade Inhibition Error—the number of reflexive saccades to the target may be higher in AD relative to the baseline or normative data.

In exemplary embodiments, the Accelerating Circle Test (described elsewhere herein) may be utilized. In exemplary embodiments, the following test results may indicate the presence of Alzheimer disease:
(1) Smooth Pursuit Gain—the smooth pursuit gain may be lower in AD relative to the baseline or normative data.

In exemplary embodiments, the Memory Test (described elsewhere herein) may be utilized. In exemplary embodiments, the following test results may indicate the presence of Alzheimer disease:
(1) Saccade Duration—the average saccade duration over all saccades in the task may be higher in AD relative to the baseline or normative data;
(2) Saccade Position—the memory saccade position error may be higher in AD relative to the baseline or normative data.

Phorias and Tropias

Tropias (T) may be characterized by diplopia as the gaze angle of the eyes may not match. Phorias (P) may be characterized in the same fashion and are found when a target is visible to only one eye. Phorias and tropias may be related to palsy or other condition that involves the alignment of the extraocular muscles. Phorias and Tropias may be diagnosed through the traditional Cover Test in which the gaze angle of both eyes is monitored with both eyes open and subsequently with one eye and then the other blocked.

Test results from one or more of the tests described elsewhere herein may indicate a presence and/or magnitude of a phoria or tropia. The result of this test may be compared to a baseline data set acquired on the same patient (herein referred to as the "baseline") or may be compared to the aggregate results of a control group (herein referred to as "normative data").

For example, in exemplary embodiments, the Phorias and Tropias test (described elsewhere herein) may be utilized. In exemplary embodiments, the following test results may indicate the presence of phoria and/or tropia:
(1) Gaze Angle Change—if the gaze angle of one or both eyes smoothly changes when one eye is covered, there may be a phoria. The magnitude and direction of the change in angle are the magnitude and direction of the phoria. If the Gaze angle changes as a saccadic movement of both eyes, there may be a tropia. The magnitude and direction of the saccadic movement are the magnitude and direction of the tropia.

Huntington Disease

Huntington Disease (HD) may be characterized by jerky movements (chorea) and psychological changes. Huntington Disease may affect the basal ganglia, thalamus, and other regions of the brain. Both physical (including MR imaging and genetic testing) and psychological testing may be used in the diagnosis of HD.

Test results from one or more of the tests described elsewhere herein may indicate a presence of Huntington Disease. The results of these tests may be compared to a baseline data set acquired on the same patient (herein referred to as the "baseline") or may be compared to the aggregate results of a control group (herein referred to as "normative data").

For example, in exemplary embodiments, the Saccadic Clock Test (described elsewhere herein) may be utilized. In exemplary embodiments, the following test results may indicate the presence of Huntington Disease:
(1) Saccade Accuracy—the accuracy of saccades (in particular the directional accuracy) may be different (e.g., lower) in HD relative to the baseline or normative data;
(2) Hypometria may occur more often in HD relative to the baseline or normative data;
(3) Hypometria may be more pronounced in the vertical direction than the horizontal in HD relative to the baseline or normative data;
(4) HD may be characterized by the presence of glissade refixation saccades after hypometria more often relative to the baseline or normative data;
(5) HD may be characterized by an increased number of premature saccades relative to the baseline or normative data;
(6) Saccade Velocity—the saccade velocity may be different (e.g., lower) in HD relative to the baseline or normative data;
(7) Saccade Latency—the saccade latency may be different (e.g., higher) in HD relative to the baseline or normative data;
(8) Saccade Latency in the vertical direction may be greater than latency in the horizontal direction in HD relative to the baseline or normative data;
(9) Saccade Latency may be more variable between measurements in HD relative to the baseline or normative data;
(10) Saccade Amplitude—the saccade amplitude variability between repeated measures at the same angle may be different (e.g., higher) in HD relative to the baseline or normative data.

In exemplary embodiments, the Central Fixation with Distraction Test (described elsewhere herein) may be utilized. In exemplary embodiments, the following test results may indicate the presence of Huntington Disease:
(1) Saccade Error—the number of saccades to the position of the distracting target may be different (e.g., higher) in HD relative to the baseline or normative data.

In exemplary embodiments, the Accelerating Circle with Distraction Test (described elsewhere herein) may be utilized. In exemplary embodiments, the following test results may indicate the presence of Huntington Disease:
(1) Smooth Pursuit Error—the smooth pursuit error may be different (e.g., higher) in HD relative to the baseline or normative data;
(2) In the presence of distraction, the smooth pursuit error may be increased further in HD relative to the baseline or normative data.

In exemplary embodiments, the Opposite Test (described elsewhere herein) may be utilized. In exemplary embodiments, the following test results may indicate the presence of Huntington Disease:

(1) Reflexive Saccade Inhibition Error—the number of reflexive saccades to the target may be different (e.g., higher) in HD relative to the baseline or normative data.

In exemplary embodiments, the Memory Test (described elsewhere herein) may be utilized. In exemplary embodiments, the following test results may indicate the presence of Huntington Disease:
(1) Saccade Duration—the average saccade duration over all saccades in the task may be different (e.g., higher) in AD relative to the baseline or normative data;
(2) Saccade Position—the memory saccade position error may be different (e.g., higher) in AD relative to the baseline or normative data.

Cranial Nerve Palsy

Cranial Nerve Palsy (CNP) may be associated with changes in the pupil response to light of the stimulated or contralateral eye or with changes in the function of the extraocular muscles. Damage to the cranial nerves or disease (such as vascular disease or multiple sclerosis) may cause cranial nerve palsies. CNP may be diagnosed by examining the extraocular and facial muscle movements in response to voluntary or reflexive stimulation.

Test results from one or more of the tests described elsewhere herein may indicate a presence of a Cranial Nerve Palsy. The results of these tests may be compared to a baseline data set acquired on the same patient (herein referred to as the "baseline") or may be compared to the aggregate results of a control group (herein referred to as "normative data").

For example, in exemplary embodiments, the Pulse Test (described elsewhere herein) may be utilized. In exemplary embodiments, the following test results may indicate the presence of Cranial Nerve Palsy:
(1) Any deviation in the ipsilateral and contralateral constriction latencies, amplitudes, and velocities or derived metrics, such as relative difference in constriction velocity between the two eyes while one eye is stimulated, may be different in CNP relative to the baseline or normative data.

In exemplary embodiments, the Saccadic Clock Test (described elsewhere herein) may be utilized. In exemplary embodiments, the following test results may indicate the presence of Cranial Nerve Palsy:
(1) Saccade Accuracy—the accuracy of saccades may be different (e.g., lower) in CNP relative to the baseline or normative data;
(2) CNP may be characterized by saccadic clock angles with little or no movement in the direction of the target, which may indicate palsy in CN III, IV, or VI, depending on the angle;
(3) Saccade Amplitude—the saccade amplitude variability between repeated measures at the same angle may be different (e.g., higher) in HD relative to the baseline or normative data;
(4) Pupil response—The amplitude of constriction of one or both pupils may be different relative to the baseline or normative data.

Multiple Sclerosis

Multiple Sclerosis (MS) is a neuro-muscular degenerative disease that leads to decreasing control of the muscular system. Multiple sclerosis may be characterized by diffuse tissue damage to the white and gray matter of the brain. MS may be difficult to diagnose and typically involves multiple test batteries including brain imaging with MRI, cerebrospinal fluid tests, and EEG.

Test results from one or more of the tests described elsewhere herein may indicate a presence of a Multiple Sclerosis. The results of these tests may be compared to a baseline data set acquired on the same patient (herein referred to as the "baseline") or may be compared to the aggregate results of a control group (herein referred to as "normative data").

For example, in exemplary embodiments the Saccadic Clock Test (described elsewhere herein) may be utilized. In exemplary embodiments, the following test results may indicate the presence of Multiple Sclerosis:
(1) Saccade Accuracy—the accuracy of saccades (in particular the directional accuracy) may be different (e.g., lower) in MS relative to the baseline or normative data.

In exemplary embodiments, the Nystagmus Test (described elsewhere herein) may be utilized. In exemplary embodiments, the following test results may indicate the presence of Multiple Sclerosis:
(1) Gaze Angle Stability—gaze angle may be more unstable in MS during central fixation relative to the baseline or normative data;
(2) The presence of skew deviation may be more likely in MS relative to the baseline or normative data.

In exemplary embodiments, the Blanked Delay Test (described elsewhere herein) may be utilized. In exemplary embodiments, the following test results may indicate the presence of Multiple Sclerosis:
(1) Saccade Errors—the number of saccade errors (saccades to the new target location rather than fixated at the first target location) may be different (e.g., higher) in MS relative to the baseline or normative data.

In exemplary embodiments, the Opposite Test (described elsewhere herein) may be utilized. In exemplary embodiments, the following test results may indicate the presence of Multiple Sclerosis:
(1) Reflexive Saccade Inhibition Error—the number of reflexive saccades to the target may be different (e.g., higher) in MS relative to the baseline or normative data.

In exemplary embodiments, the Memory Test (described elsewhere herein) may be utilized. In exemplary embodiments, the following test results may indicate the presence of Multiple Sclerosis:
(1) Saccade Duration—the average saccade duration over all saccades in the task may be different (e.g., higher) in MS relative to the baseline or normative data;
(2) Saccade Position—the memory saccade position error may be different (e.g., higher) in AD relative to the baseline or normative data.

Myasthenia Gravis

Myasthenia Gravis (MG) is a neuromuscular disorder that may be characterized by muscle weakness and fatigue that may be caused by an auto-immune reaction that suppresses acetylcholine receptors at the neuromuscular junction. MG may be diagnosed through a thorough physical exam and blood tests.

Test results from one or more of the tests described elsewhere herein may indicate a presence of Myasthenia Gravis. The results of these tests may be compared to a baseline data set acquired on the same patient (herein referred to as the "baseline") or may be compared to the aggregate results of a control group (herein referred to as "normative data").

For example, in exemplary embodiments, the Saccadic Clock Test (described elsewhere herein) may be utilized. In exemplary embodiments, the following test results may indicate the presence of Myasthenia Gravis:

1) Saccade Accuracy—the accuracy of saccades (in particular the directional accuracy) may be different (e.g., lower) in Myasthenia Gravis relative to the baseline or normative data;
   a) Hypometria after repeated saccades may occur more often in Myasthenia Gravis relative to the baseline or normative data;
   b) Saccade refixation is more likely to be characterized by glissades in Myasthenia Gravis relative to the baseline or normative data.

In exemplary embodiments, the Nystagmus Test (described elsewhere herein) may be utilized. In exemplary embodiments, the following test results may indicate the presence of Myasthenia Gravis:
1) When viewing a stationary target, a central gaze-evoked nystagmus is more likely to appear in Myasthenia Gravis relative to the baseline or normative data;
2) When looking at a stationary target in the lower visual field, the upper eye lid is more likely to start twitching (a phenomenon known as Crogan's lid twitch) in Myasthenia Gravis relative to the baseline or normative data.

Schizophrenia

Schizophrenia may be characterized by emotional or behavioral changes. Schizophrenia is a mental illness whose root cause is not well understood. Schizophrenia may be diagnosed through psychiatric evaluation.

Test results from one or more of the tests described elsewhere herein may indicate a presence of Schizophrenia. The results of these tests may be compared to a baseline data set acquired on the same patient (herein referred to as the "baseline") or may be compared to the aggregate results of a control group (herein referred to as "normative data").

For example, in exemplary embodiments, the Saccadic Clock Test (described elsewhere herein) may be utilized. In exemplary embodiments, the following test results may indicate the presence of Schizophrenia:
(1) Saccade Accuracy—the accuracy of saccades (in particular the directional accuracy) may be different (e.g., lower) in Schizophrenia relative to the baseline or normative data;
(2) Hypometria may occur more often in Schizophrenia relative to the baseline or normative data;
(3) Hypometria may be more pronounced in the horizontal direction than the vertical in Schizophrenia relative to the baseline or normative data.

In exemplary embodiments, the Opposite Test (described elsewhere herein) may be utilized. In exemplary embodiments, the following test results may indicate the presence of Schizophrenia:
(1) Reflexive Saccade Inhibition Error—the number of reflexive saccades to the target may be different (e.g., higher) in Schizophrenia relative to the baseline or normative data.

In exemplary embodiments, the Memory Test (described elsewhere herein) may be utilized. In exemplary embodiments, the following test results may indicate the presence of Schizophrenia:
(1) Saccade Position—the memory saccade position error may be different (e.g., higher) in Schizophrenia relative to the baseline or normative data.

In exemplary embodiments, the Accelerating Circle Test (described elsewhere herein) may be utilized. In exemplary embodiments, the following test results may indicate the presence of Schizophrenia:
(1) Smooth Pursuit Breakdown Speed—the velocity at which smooth pursuit breaks into saccades may be different (e.g., lower) in Schizophrenia relative to the baseline or normative data;
(2) Smooth Pursuit Error—the smooth pursuit error may be different (e.g., higher) in Schizophrenia relative to the baseline or normative data;
(3) Smooth Pursuit Gain—the smooth pursuit gain may be different (e.g., lower) in Schizophrenia relative to the baseline or normative data.

Intoxication

Intoxication from alcohol or other drugs can have a marked effect physical and mental state, including slowed response time, slurred speech, double or blurred vision, and emotional distress. Alcohol and other intoxicating substances affect the brain in various ways. Alcohol, ethanol in particular, may affect glutamate-binding receptors in the brain. Alcohol intoxication may be diagnosed via physical or mental acuity tests as well as a blood alcohol test. Other forms of intoxication may be diagnosed through similar means.

Test results from one or more of the tests described elsewhere herein may indicate a presence of Intoxication. The results of these tests may be compared to a baseline data set acquired on the same patient (herein referred to as the "baseline") or may be compared to the aggregate results of a control group (herein referred to as "normative data").

For example, in exemplary embodiments, the Saccadic Clock Test (described elsewhere herein) may be utilized. In exemplary embodiments, the following test results may indicate the presence of Intoxication:
(1) Saccade Accuracy—the accuracy of saccades may be different (e.g., lower) in Intoxication relative to the baseline or normative data;
(2) Saccade refixation is more likely to characterized by glissades in Intoxication relative to the baseline or normative data;
(3) Saccade Velocity—the saccade velocity may be different (e.g., lower) in Intoxication relative to the baseline or normative data;
(4) Saccade Latency—the saccade latency bye be different (e.g., higher) in Intoxication relative to the baseline or normative data.

In exemplary embodiments, the Main Sequence (described elsewhere herein) may be utilized. In exemplary embodiments, the following test results may indicate the presence of Intoxication:
(1) Saccade Accuracy—the accuracy of saccades may be different (e.g., lower) in Intoxication relative to the baseline or normative data;
(2) Saccade refixation is more likely to characterized by glissades in Intoxication relative to the baseline or noremative data;
(3) Saccade Velocity—the saccade velocity may be different (e.g., lower) in Intoxication relative to the baseline or normative data;
(4) Saccade Latency—the saccade latency may be different (e.g., higher) in Intoxication relative to the baseline or normative data.

In exemplary embodiments, the Accelerating Circle Test (described elsewhere herein) may be utilized. In exemplary embodiments, the following test results may indicate the presence of Intoxication:
(1) Smooth Pursuit Breakdown Speed—the velocity at which smooth pursuit breaks into saccades may be different (e.g., lower) in Intoxication relative to the baseline or normative data;

(2) Smooth Pursuit Error—the smooth pursuit error may be different (e.g., higher) in Intoxication relative to the baseline or normative data;

(3) Smooth Pursuit Gain—the smooth pursuit gain may be different (e.g., lower) in Intoxication relative to the baseline or normative data.

In exemplary embodiments, the Pupil Response to Convergence Test (described elsewhere herein) may be utilized. In exemplary embodiments, the following test results may indicate the presence of Intoxication:

(1) Gaze Angle—the mean error in gaze angle may be different (e.g., higher) in Intoxication relative to the baseline or normative data;

(2) Convergence Distance—the closest distance for which smooth convergence occurs may be different in Intoxication relative to the baseline or normative data.

In exemplary embodiments, the Pulse Test (described elsewhere herein) may be utilized. In exemplary embodiments, the following test results may indicate the presence of Intoxication:

(1) Any deviation in the reflexive and consensual constriction and subsequent dilation latencies, amplitudes, and velocities or derived metrics, such as relative difference in constriction velocity between the two eyes while one eye is stimulated, may be different in Intoxication relative to the baseline or normative data;

(2) Intoxication may be characterized by a slower response to light stimulus or less constriction during light stimulus relative to the baseline or normative data.

Fatigue

Fatigue may be characterized by decreased reaction times, change in emotional state, loss of appetite, or slowed reflexes. Physical or mental fatigue may be caused by over-exertion or lack of sleep. The cause of fatigue may be diagnosed through a mental or physical exam and may involve blood tests.

Test results from one or more of the tests described elsewhere herein may indicate a presence of Fatigue. The results of these tests may be compared to a baseline data set acquired on the same patient (herein referred to as the "baseline") or may be compared to the aggregate results of a control group (herein referred to as "normative data").

For example, in exemplary embodiments, the Saccadic Clock Test (described elsewhere herein) may be utilized. In exemplary embodiments, the following test results may indicate the presence of Fatigue:

(1) Saccade Accuracy—the accuracy of saccades may be different (e.g., lower) in Fatigue relative to the baseline or normative data;

(2) Saccade refixation is more likely to characterized by glissades in Fatigue relative to the baseline or normative data;

(3) Saccade Velocity—the saccade velocity may be different (e.g., lower) in Fatigue relative to the baseline or normative data;

(4) Saccade Latency—the saccade latency may be different (e.g., higher) in Fatigue relative to the baseline or normative data.

In exemplary embodiments, the Pulse Test (described elsewhere herein (e.g., the RAPD test)) may be utilized. In exemplary embodiments, the following test results may indicate the presence of Fatigue:

(1) Any deviation in the reflexive and consensual constriction and subsequent dilation latencies, amplitudes, and velocities or derived metrics, such as relative difference in constriction velocity between the two eyes while one eye is stimulated, may be different in Fatigue relative to the baseline or normative data;

(2) Fatigue may be characterized by increased constriction relative to a baseline non-fatigued state, with constriction being greater with increasing fatigue;

(3) Fatigue may be indicated by a change in the velocity of dilation between flashes.

While exemplary embodiments have been shown and described herein, it will be obvious to those skilled in the art that such embodiments are provided by way of example only. It is intended that the following claims define the scope of the invention and that methods and structures within the scope of these claims and their equivalents be covered thereby.

What is claimed is:

1. A device for monitoring eye movement and pupil response, the device comprising:
   a first optical pathway for displaying an image to the eyes of a patient;
   a second optical pathway for obtaining an image of the eyes of a patient;
   at least one screen for displaying an image to the left eye of the patient which is not visible to the right eye of the patient and for displaying an image to the right eye of the patient which is not visible to the left eye of the patient;
   a first camera for capturing images of the left eye of the patient;
   a second camera for capturing images of the right eye of the patient, at substantially the same time as the first camera is capturing images of the left eye of the patient;
   at least one IR light source for illuminating the eyes of the patient; and
   a processor for processing the obtained images and measuring pupil response and eye movements and comparing the pupil response and eye movements to similar data obtained from the same patient as a baseline measurement;
   wherein measuring pupil response comprises measuring a pupil diameter and a rate of change of the pupil diameter.

2. The device of claim 1, wherein pupil response comprises looking at the size of both pupils to determine how well the pupil responses are synchronized.

3. The device of claim 1, wherein the processing further comprises determining the latency of the pupil response and/or eye movements.

4. The device of claim 1, wherein the processing further comprises determining the acceleration of the pupil response and/or eye movements.

5. The device of claim 1, wherein the processing further comprises distinguishing between translations and rotations of the eye.

6. The device of claim 1, wherein the device is capable of simulating macular degeneration.

7. The device of claim 1, wherein the processor uses Hough transforms to track eye movements.

8. The device of claim 1, further comprising at least one memory for storing a catalog of pathologies.

9. The device of claim 1, wherein the processor is configured to measure the relative sensitivities of the left and right retinas of the eyes.

10. The device of claim 1, wherein the processor is configured to measure the maximum velocity of pupil restriction.

11. The device of claim 1, wherein the processor is configured to measure the differences between predetermined properties and/or responses of the pupils.

12. The device of claim 1, wherein the processor is configured to compare predetermined properties of pupils to a set of predetermined population data.

13. The device of claim 1, wherein the processor is configured to compare the pupil response to convergence to a set of predetermined population data.

14. The device of claim 1, wherein the processor is configured to detect floppy iris.

15. The device of claim 1, wherein the processor is configured to compare pupil perimetry data to a set of predetermined population data.

16. The device of claim 1, wherein the device is configured to perform a fatigue test separately for each eye.

17. The device of claim 1, wherein the device is configured to measure and/or detect any plurality of the following: amplitude of a saccadic movement, maximum velocity of a saccadic movement, latency of a saccadic movement, accuracy of a saccadic movement, and/or direction of a saccadic movement.

18. The device of claim 1, wherein the device is configured to provide a target which moves in a predetermined pattern while measuring the smoothness with which the eyes track the target.

19. The device of claim 1, wherein the device is configured to measure the amount of scattering of light attributable to cataracts in the eye.

20. A device for identifying concussions, the device comprising:
a first optical pathway for displaying an image to the eyes of a patient;
a second optical pathway for obtaining an image of the eyes of a patient;
at least one screen for displaying an image to the left eye of the patient which is not visible to the right eye of the patient and for displaying an image to the right eye of the patient which is not visible to the left eye of the patient;
a first camera for capturing images of the left eye of the patient and for capturing images of the right eye of the patient, at substantially the same time;
at least one IR light source for illuminating the eyes of the patient; and
a processor for processing the obtained images and measuring pupil response and eye movements and comparing the pupil response and eye movements to similar data obtained from the same patient as a baseline measurement, wherein the processor is further configured to identify in substantially real-time whether the patient has a concussion based on predetermined differences between the baseline measurement and the current measurements;
wherein measuring pupil response comprises measuring a pupil diameter and a rate of change of the pupil diameter.

21. The device of claim 20, wherein the device is configured to use the camera to capture images of only one eye at a time.

22. The device of claim 20, further comprising a second camera, wherein the first camera is configured to capture an image of one eye and the second camera is configured to capture an image of the second eye, at substantially the same time.

* * * * *